US011628132B2

(12) United States Patent
Goren et al.

(10) Patent No.: US 11,628,132 B2
(45) Date of Patent: Apr. 18, 2023

(54) MINOXIDIL ADJUVANT THERAPIES

(71) Applicant: JUPITER WELLNESS, INC., Jupiter, FL (US)

(72) Inventors: Ofer A. Goren, Irvine, CA (US); John McCoy, Irvine, CA (US)

(73) Assignee: JUPITER WELLNESS, INC., Jupiter, FL (US)

( * ) Notice: Subject to any disclaimer, the term of this patent is extended or adjusted under 35 U.S.C. 154(b) by 0 days.

(21) Appl. No.: 16/747,685

(22) Filed: Jan. 21, 2020

(65) Prior Publication Data

US 2020/0214958 A1 Jul. 9, 2020

Related U.S. Application Data

(63) Continuation-in-part of application No. 16/593,577, filed on Oct. 4, 2019.

(60) Provisional application No. 62/895,627, filed on Sep. 4, 2019, provisional application No. 62/849,598, filed on May 17, 2019, provisional application No. 62/800,065, filed on Feb. 1, 2019, provisional application No. 62/756,293, filed on Nov. 6, 2018, provisional application No. 62/741,990, filed on Oct. 5, 2018.

(51) Int. Cl.
```
A61K 8/49       (2006.01)
A61K 8/14       (2006.01)
A61Q 7/00       (2006.01)
A61K 31/506     (2006.01)
A61K 9/127      (2006.01)
A61P 17/14      (2006.01)
A61K 31/353     (2006.01)
A61K 31/122     (2006.01)
A61K 8/35       (2006.01)
```

(52) U.S. Cl.
CPC .............. *A61K 8/4953* (2013.01); *A61K 8/14* (2013.01); *A61K 8/35* (2013.01); *A61K 8/355* (2013.01); *A61K 8/498* (2013.01); *A61K 9/127* (2013.01); *A61K 31/122* (2013.01); *A61K 31/353* (2013.01); *A61K 31/506* (2013.01); *A61P 17/14* (2018.01); *A61Q 7/00* (2013.01); *A61K 2800/5922* (2013.01); *A61K 2800/78* (2013.01)

(58) Field of Classification Search
None
See application file for complete search history.

(56) References Cited

U.S. PATENT DOCUMENTS

| | | | |
|---|---|---|---|
| 5,360,804 A | 11/1994 | Gaetani et al. | |
| 5,373,006 A | 12/1994 | Grollier | |
| 5,384,126 A * | 1/1995 | Bonte | A61K 36/53 424/450 |
| 2003/0007941 A1 | 1/2003 | Cornelius et al. | |
| 2009/0214628 A1 | 8/2009 | de Rijk | |
| 2016/0220465 A1* | 8/2016 | Goren | A61K 8/046 |

OTHER PUBLICATIONS

Non-Final Office Action for U.S. Appl. No. 16/593,577 dated Sep. 23, 2020.
Admin, title: pH of the skin and Body—The Science Responsible for Life; published Nov. 20, 2017; downloaded from https://www.stlouishair.com/ph-of-the-skin-and-body-the-science-responsible-for-life/(year:2017).
Dooley, T, P.; Localization of Minoxidil Sulfotransferase in Rat Liver and the Outer Root Sheath of Anagen Pelage and Vibrissa Follicles, The Journal of Investigative Dermatology, 1991, 65-70, The Society for Investigative Dermatology, Inc.
Bryant et al., "Here's What You Need to Know About the Latest Korean Beauty Obsession," *Scalp PH Facts—PH Balanced Shampoo Products*, 4 pages, (2016).

* cited by examiner

*Primary Examiner* — Robert A Wax
*Assistant Examiner* — Quanglong N Truong
(74) *Attorney, Agent, or Firm* — Hoxie & Associates LLC

(57) ABSTRACT

Compositions and methods are disclosed herein for inducing (up-regulating) the expression of sulfotransferases in the hair follicles, e.g., the scalp. Increasing sulfotransferase is beneficial for metabolizing pro-drugs that require sulfonation to be activated, e.g., minoxidil sulfate is the active metabolite of minoxidil. A method for combining the compositions described herein with topical minoxidil to enhance minoxidil treatment for androgenetic alopecia is described. Additional methods and compositions include the use of retinoid X receptor agonists, retinoic acid receptor agonists, and nuclear receptor agonists in an RXR—NR heterodimer. Additional methods and compositions include the use of a topical solution containing an alkalinizing agent or an alkalinizing agent used with a penetration enhancer for upregulating the sulfonating capacity of hair bearing skin, hair follicles, and/or keratinocyte cells. In addition, compositions and methods for increasing or decreasing the growth rate of hair follicles is disclosed by altering the intracellular pH.

17 Claims, 9 Drawing Sheets

Week 16 - Blinded Expert Assessment
tabulated expert assessment at week 16

|  | Comparator n(%) | Treatment n(%) |
|---|---|---|
| Score |  |  |
| 0 | 10 (52%) | 4 (25%) |
| 1 | 6 (32%) | 5 (31%) |
| 2 | 3 (16%) | 5 (31%) |
| 3 | 0 (0%) | 2 (13%) |

Graph of global photography assessment score by treatment arm

Comparator Placebo

Sulfotransferase enzyme activity (OD) in the AB-103 group and placebo group following a 7 day treatment regimen

| Subject Nr. | AB-103 | | | Placebo | | |
|---|---|---|---|---|---|---|
| | OD (D0) | OD (D7) | OD (D7-D0) | OD (D0) | OD (D7) | OD (D7-D0) |
| 001 | 0.438 | 0.733 | 0.295 | 0.329 | 0.462 | 0.133 |
| 002 | 0.401 | 0.758 | 0.357 | 0.379 | 0.409 | 0.030 |
| 003 | 0.528 | 1.040 | 0.512 | 0.387 | 0.275 | -0.112 |
| 004 | 0.610 | 0.935 | 0.325 | 0.456 | 0.554 | 0.098 |
| 005 | 0.590 | 0.882 | 0.292 | 0.476 | 0.414 | -0.062 |
| 006 | 0.639 | 0.692 | 0.053 | 0.626 | 0.446 | -0.180 |
| 007 | 0.662 | 0.514 | -0.148 | 0.662 | 0.733 | 0.071 |
| 008 | 0.729 | 0.999 | 0.270 | 0.757 | 0.744 | -0.014 |
| 009 | 0.764 | 1.381 | 0.618 | 0.856 | 0.724 | -0.132 |
| 010 | 0.876 | 0.714 | -0.161 | 0.902 | 0.985 | 0.083 |

Mean change in follicular sulfotransferase activity by treatment group. AB_103=AB-103 shampoo, Placebo=vehicle shampoo Week 24 - Blinded Expert Assessment
tabulated expert assessment at week 24

|  | Minoxidil n(%) | AB-103 + Minoxidil n(%) |
|---|---|---|
| Score |  |  |
| -1 | 1 (6%) | 1 (6%) |
| 0 | 9 (60%) | 4 (26%) |
| 1 | 3 (20%) | 6 (40%) |
| 2 | 2 (13%) | 2 (13%) |
| 3 | 0 (0%) | 2 (13%) |

Expert assessment graph by treatment group. MX=minoxidil monotherapy, AB_MX=AB-103+minoxidil Mean Change in TAHC - week 24

| Treatment Group | N | Mean (SD) |
|---|---|---|
| AB-103 + MX | 14 | 12.9 (9.4) |
| Placebo | 12 | 3.0 (8.0) |

Mean change in TAHC at week 24. Placebo=vehicle shampoo+minoxidil, AB_103=AB-103+minoxidil.

| Subject | Assay Color (Green, Yellow, Blue) | Indicated pH (<6.0, 6.0-7.6, >7.6) | Image |
|---|---|---|---|
| AB-001 | Yellow | < 6.0 |  |
| AB-002 | Yellow | < 6.0 |  |

Table 5. Assay results for pHi of HFSC niche in hair follicles.

| Subject | Assay Color (Green, Yellow, Blue) | Indicated pH (<6.0, 6.0-7.6, >7.6) | Image |
|---|---|---|---|
| AB-021 | Yellow | < 6.0 | |
| AB-022 | Yellow | < 6.0 | |

Table 8. Time 0 (zero).

FIG. 6

| Subject | Assay Color (Green, Yellow, Blue) | Indicated pH (<6.0, 6.0-7.6, >7.6) | Image |
|---|---|---|---|
| AB-021 | Green | 6.0 – 7.6 |  |
| AB-022 | Green | 6.0 – 7.6 |  |

Table 9. 15 min.

| Subject | Assay Color (Green, Yellow, Blue) | Indicated pH (<6.0, 6.0-7.6, >7.6) | Image |
|---|---|---|---|
| AB-021 | Blue | > 7.6 |  |
| AB-022 | Blue | > 7.6 |  |

Table 10. 30 min.

MINOXIDIL ADJUVANT THERAPIES

CROSS-REFERENCE TO RELATED APPLICATIONS

This application is a continuation-in-part application of U.S. Ser. No. 16/593,577, filed on Oct. 4, 2019, the U.S. Ser. No. 16/593,577 application being related to and claiming the benefit of MINOXIDIL ADJUVANT THERAPIES, filed on Oct. 5, 2018 and issued Application No. 62/741,990, MINOXIDIL ADJUVANT THERAPIES, filed on Nov. 6, 2018 and issued Application No. 62/756,293, MINOXIDIL ADJUVANT THERAPIES, filed on Feb. 1, 2019 and issued Application No. 62/800,065, MINOXIDIL ADJUVANT THERAPIES, filed on May 17, 2019 and issued Application No. 62/849,598, and MINOXIDIL ADJUVANT THERAPIES, filed on Sep. 4, 2019 and issued Application No. 62/895,627, the entire contents of each being incorporated herein by reference in their entirety.

FIELD

The present invention relates to methods and compositions that induce the expression of sulfotransferase in the hair follicle. Topical compositions containing agents that bind to the transcription factors that mediate the xenobiotic response in cells (e.g., PDX and CAR) are described. Up-regulation of sulfotransferase is beneficial to activate certain prodrugs that require sulfonation to become activated. One such drug is minoxidil used to treat androgenetic alopecia. The present invention is directed to methods for treating, reducing or preventing alopecia and other hair loss disorders by applying a sulfotransferase inducing composition on the scalp prior to treatment with minoxidil. Additional embodiments relate to compositions and kits that diagnose and control hair follicle stem cell differentiation. Methods and compositions are described that modify hair follicle stem cells intracellular pH thus controlling hair follicle stem cell differentiation. In some instances, increase of hair follicle stem cells intracellular pH induces and/or increases the sulfotrasnfrease enzymatic activity in hair follicle cells. Induction of the sulfotransferase enzyme in hair follicles increases the sulfonation capacity of minoxidil; thus, increasing the response level to oral and topical minoxidil in the treatment of alopecia.

BACKGROUND

In 1988 the US FDA approved 2% topical minoxidil solution as an OTC drug for the treatment of androgenetic alopecia (AGA). Since the FDA approval, minoxidil has become the mainstay therapy for AGA. However, the effectiveness of minoxidil in the general population is low, only 39% of patients respond to the drug (See Olsen E A, Whiting D, Bergfeld W, Miller J, Hordinsky M, Wanser R, et al. A multicenter, randomized, placebo-controlled, double-blind clinical trial of a novel formulation of 5% minoxidil topical foam versus placebo in the treatment of androgenetic alopecia in men. J Am Acad Dermatol. 2007 57(5): 767-74). In the pivotal study submitted to the US FDA in support of the efficacy of the 5% topical minoxidil foam, no subjects had great improvement, 8% of the subjects had a moderate improvement, and 31% of the subjects had a slight improvement (See US FDA Application 21-812 Medical Review).

Minoxidil is a pro-drug converted to its active form, minoxidil sulfate, by sulfotransferase enzymes present in the outer root sheath (ORS) of hair follicles (See Buhl A E, Waldon D J, Baker C A, Johnson G A. Minoxidil sulfate is the active metabolite that stimulates hair follicles. J Invest Dermatol. 1990 November; 95(5):553-7). It has been demonstrated that the activity of sulfotransferase in the ORS determines the clinical response to minoxidil (See Goren A, Castano J A, McCoy J, Bermudez F, Lotti T. Novel enzymatic assay predicts minoxidil response in the treatment of androgenetic alopecia. Dermatol Ther. 2014; 27(3):171-3). Sulfotransferase enzymes are expressed in abundance in the human liver. In the human liver, sulfotransferase is part of the Phase II enzymatic system that reduces xenobiotic toxicity (See Jancova P, Anzenbacher P, Anzenbacherova E. Phase II drug metabolizing enzymes. Biomed Pap Med Fac Univ Palacky Olomouc Czech Repub. 2010; 154(2):103-16).

Xenobiotics are extrinsic chemical substances (e.g., drugs), which may be present in human body (See Croom E. Metabolism of xenobiotics of human environments. Prog Mol Biol Transl Sci 2012; 112: 31-88). They are included into specific metabolic pathways evolved to mitigate toxicity to an organism. Xenobiotic metabolism includes several pathways designed to modify chemical structure and decrease the toxicity of the compounds. Although, in some instances, the intermediates in xenobiotic metabolism may themselves cause toxic effects (See Bunchorntavakul C, Reddy K R. Acetaminophen (APAP or N-Acetyl-p-Aminophenol) and Acute Liver Failure. Clinics in Liver Disease 2018; 22(2): 325-346). Xenobiotic metabolism is divided into 3 phases, organized to modify lipophilic compounds into hydrophilic conjugates that can more readily be excreted. In Phase I, lipophilic xenobiotic molecules are metabolized by enzymes such as cytochrome P450 oxidases, which introduce polar groups and provide sites for downstream conjugation reactions. Phase I reactions are mainly localized in the liver. In Phase II, conjugating enzymes interact with metabolites produced by Phase I enzymes and eliminate them through both passive and active transport. Conjugating enzymes include a large group of broad-specificity transferases, with glutathione S-transferases as the most important representatives (See Jakoby W B, Ziegler D M. The enzymes of detoxication. J Biol Chem 1990; 265 (34): 20715-20718). After conjugation, any xenobiotic conjugates or their metabolites not eliminated in Phase II are further processed and eliminated in Phase III by transporter proteins.

Several Phase I and II metabolizing enzymes are known to be inducible by both endogenous and xenobiotic molecules. The most widely studied drug-metabolizing enzyme, by far, is the cytochrome P450 family. Many of the members of the cytochrome P450 family are inducible via nuclear receptor mediated induction. For example, cytochrome family 1 genes are up-regulated by the aryl hydrocarbon receptor (AhR) after it binds aromatic hydrocarbon ligands (See Gonzalez F J, Liu S Y, Yano M. Regulation of cytochrome P450 genes: molecular mechanisms. Pharmacogenetics 1993; 3(1): 51-57). Similarly, sulfotransferases have been demonstrated to be regulated by endogenous hormones (See Runge-Morris M, Kocarek T A, Falany C N. Regulation of the cytosolic sulfotransferases by nuclear receptors. Drug metabolism reviews 2013; 45(1): 15-33) and xenobiotics (See Runge-Morris M, Kocarek T A. Regulation of sulfotransferases by xenobiotic receptors. Curr Drug Metab 2005; 6(4): 299-307).

Minoxidil sulfate is required for both the promotion of hair regrowth and the vasodilatory effects of minoxidil. Sulfotransferase enzymes are located in both the skin and the liver and are important Phase II xenobiotic metabolizing enzymes for a number of phenolic molecules including minoxidil (See Nimmagadda D, Cherala G, Ghatta S. Cytosolic sulfotransferases. Indian J Exp Biol 2006; 44(3): 171-182).

Xenobiotic-metabolizing enzymes are important for the metabolism, elimination or detoxification of xenobiotics. Various nuclear receptors including aryl hydrocarbon receptor (AhR) and constitutive androstane receptor (CAR) regulate the gene expressions of Xenobiotic-metabolizing enzymes (See Xu, C., Li, C. Y., Kong, A. N., 2005. Induction of phase I, II and III drug metabolism/transport by xenobiotics. Arch. Pharm. Res. 28, 249-268). Upon ligand binding, AhR forms a heterodimer with the AhR nuclear translocator (Arnt), and the AhR-Arnt complex binds to specific xenobiotic responsive elements and activates a battery of genes including members of cytochrome P450 family 1 (CYP1), such as CYP1A1, CYP1A2, CYP1B1, and UDP-glucuronosyltransferases (UGT) 1A1, 1A6, 1A7 and 1A9 involved in the detoxification and elimination of xenobiotics as well as certain endogenous steroids. CAR and pregnane X receptor (PXR) are nuclear receptors that form functional heterodimers with the retinoid X receptor (RXR) (See Honkakoski, P., Sueyoshi, T., Negishi, M., 2003. Drug-activated nuclear receptors CAR and PXR. Ann. Med. 35, 172-182). CAR and PXR are responsible for the xenobiotic-mediated induction of many genes including CYP1A, 2B, 2C and 3A families, UGT1A1 and 1A3, and sulfotransferase (SULT) 1A1 and 2A1 (See Handschin, C., Meyer, U. A., 2003. Induction of drug metabolism: the role of nuclear receptors. Pharmacol. Rev. 55, 649-673 and Maglich, J. M., Stoltz, C. M., Goodwin, B., Hawkins-Brown, D., Moore, J. T., Kliewer, S. A., 2002. Nuclear pregnane x receptor and constitutive androstane receptor regulate overlapping but distinct sets of genes involved in xenobiotic detoxification. Mol. Pharmacol. 62, 638-646). Additionally, 3'-phosphoadenosine 5'-phosphosulfate (PAPS) synthase (PAPSS), which catalyzes the biosynthesis of PAPS, which serves as the universal sulfonate donor compound for all sulfotransferase reactions is regulated by PXR and CAR (See Owen B M, Milona A, van Mil S, Clements P, Holder J, Boudjelal M, Cairns W, Parker M, White R, Williamson C. Intestinal detoxification limits the activation of hepatic pregnane X receptor by lithocholic acid. Drug Metab Dispos. 2010 January; 38(1):143-9. and Alnouti Y, Klaassen C D. Regulation of sulfotransferase enzymes by prototypical microsomal enzyme inducers in mice. J Pharmacol Exp Ther. 2008 February; 324(2):612-21).

Many compounds have been reported to bind to nuclear factors and induce or suppress the expression of xenobiotic-metabolizing enzymes. For a comprehensive list See A. Parkinson, B. W. Ogilvie, D. B. Buckley, F. Kazmi, M. Czerwinski, O. Parkinson, Biotransformation of xenobiotics, in: C. Klaassen (Ed.), Casarett & Doull's Toxicology, The Basic Science of Poisons, McGraw-Hill Education, New York, N.Y., USA, 2013, pp. 185-366.

Additionally, altering intracellular or extracellular pH is an important regulatory mechanism, which can influence cellular function and lead to cell differentiation in a range of stem cells (See Charruyer A, Ghadially R. Influence of pH on Skin Stem Cells and Their Differentiation. Curr Probl Dermatol. 2018; 54: 71-78). Cell differentiation is associated with the altered expression of many proteins including xenobiotic-metabolizing enzymes. Specifically, increased sulfotransferase is a marker for keratinocyte differentiation (See, Johnson G A, Baker C A, Knight K A. Minoxidil sulfotransferase, a marker of human keratinocyte differentiation. J Invest Dermatol. 1992 May; 98(5): 730-3).

All studies to date exploring nuclear factors ability to induce or suppress the expression of xenobiotic-metabolizing enzymes have been conducted in cultured liver cells, cultured colon cells, or in mice. In order to determine the induction of xenobiotic-metabolizing enzymes in scalp tissues new methodologies will need to be employed. One such technology is a colorimetric assay for detecting sulfotransferase in plucked hair samples described in U.S. Pat. No. 8,691,518, which is incorporated herein in its entirety by reference.

SUMMARY

Compositions and methods are disclosed herein for inducing (up-regulating) the expression of sulfotransferases in hair bearing skin, hair follicles, and/or keratinocyte cells, e.g., the scalp. In addition, compositions, methods, and kits are disclosed herein for controlling hair follicle stem cell differentiation. In some instances, the compositions and methods induce (up-regulate) the expression or activity of sulfotransferases in hair bearing skin, hair follicles, and/or keratinocyte cells. Increasing sulfotransferase is beneficial for metabolizing pro-drugs that require sulfonation to be activated, e.g., minoxidil sulfate is the active metabolite of minoxidil. Combining the composition described herein with topical minoxidil would be a more efficacious treatment for androgenetic alopecia. For example, embodiments of the methods and compositions disclosed herein can be used to increase the metabolism of minoxidil (which can result in the increase of bioavailable minioxidil sulfate) in hair follicles of patients suffering from a form of alopecia. Additionally, an example of a topical composition, a shampoo, used to increase sulfotransferase in the scalp is described. In other instances, the compositions and methods alter the hair follicle stem cells pH and thus slows hair growth. This can be beneficial to slow normal hair growth so people could shave less frequently.

BRIEF DESCRIPTION OF THE DRAWINGS

FIGS. 6-8 are tables showing results of a study assessing the ability to change HFSC pHi.

DETAILED DESCRIPTION

Figure 1:
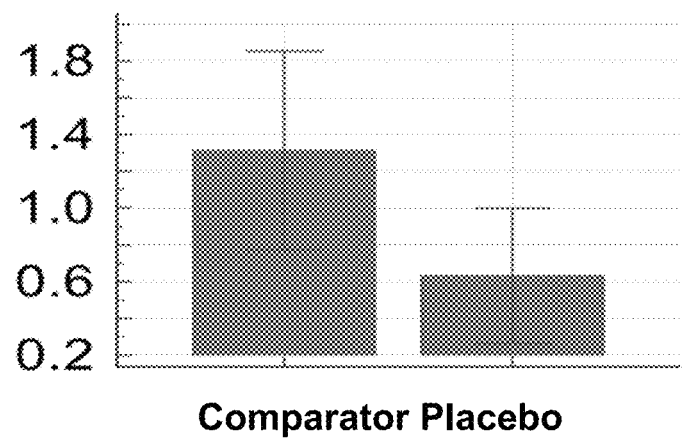
FIG. 1 is tabulated assessment of data and a global photography assessment graph related to a study conducted to evaluate an embodiment of AB-103 as an adjuvant therapy.

Androgenetic alopecia (AGA) is a common dermatological condition affecting approximately 50% of the population by the age of 50. Currently, the only drug approved by the US Food and Drug Administration (FDA) for the treatment of AGA in both men and women is topical minoxidil. Clinical trials have demonstrated that following 16 weeks of 5% minoxidil therapy approximately 30-40% of patients regrow hair.

While the exact mechanism of action of minoxidil in the treatment of AGA is not completely understood, research has demonstrated that minoxidil sulfate is the active compound that stimulates hair follicles. Minoxidil is converted to its active form, minoxidil sulfate, in the outer root sheath of the hair follicle by endogenous sulfotransferase enzymes utilizing 3'-phosphoadenosine 5'-phosphosulfate (PAPS). PAPS is produced in cells utilizing 3'-phosphoadenosine 5'-phosphosulfate synthase (PAPSS). Several studies have reported a correlation between sulfotransferase activity in plucked hair follicles and minoxidil response for AGA patients. In theory, increasing sulfotransferase or PAPS in the scalp would increase the likelihood that a subject will respond to topical minoxidil (thereby increasing the efficacy of a topical minoxidil); however, this has not been demonstrated in clinical studies. Further, in medicine, the induction of a deficient enzyme frequently does not result in a clinical benefit. For example, the pro-drug acyclovir used for the treatment of HSV is activated by the human thymidine kinase enzyme; however, while the induction of the thymidine kinase enzyme in-vitro activates acyclovir, in human studies thymidine kinase enzyme induction does not convert non-responders to acyclovir into responders. As noted herein, minoxidil compositions can be used to treat forms of alopecia. Thus, increasing the efficacy of minoxidil (which can involve converting androgenetic alopecia patients who are non-responders into responders to minoxidil) can improve hair growth (inclosing hair diameter) of subjects using topical minoxidil. In addition, methods and compositions disclosed herein for increasing the efficacy of minoxidil for treatment of forms of alopecia can accelerate hair growth of subjects using topical minoxidil.

Biological sulfation is the conversion of the very stable oxy-anion sulfate to the high-energy sulfate donor 3'-phospho-adenosine-5'-phosphosulphate (PAPS). Sulfation of a variety of biomolecules depend on availability of the precursor PAPS, which is rate-limiting. In mammals, PAPS is synthesized in two steps by a bi-functional enzyme called PAPS synthetase (PAPSS). The synthesis of PAPS from inorganic sulfate and ATP is catalyzed by PAPSS. The sources of inorganic sulfur in nature are broad but include cysteine, 1-cysteine, hydrogen sulfide, elemental sulfur, sulfite, thiosulfate, and various polythionates (e.g., tetrathionate).

In one embodiment, the invention concerns up-regulating the sulfonating capacity of hair bearing skin by applying a topical solution containing a source of inorganic sulfur to increase the concentration of PAPS. Examples of sources of inorganic sulfur include but are not limited to cysteine, 1-cysteine, hydrogen sulfide, elemental sulfur, sulfite, thiosulfate, and various polythionates (e.g., tetrathionate). Additionally, a sulfate salt may be used, for example magnesium sulfate or sodium sulfate.

As used herein, the terms "prevent" or "prevention" and other derivatives of the words, when used in reference to alopecia, e.g., androgenetic alopecia, refer to a reduced likelihood of alopecia in an individual receiving a given treatment relative to that of a similar individual at risk for alopecia but not receiving that treatment. As such, the terms "prevent" and "prevention" encompass a treatment that results in a lesser degree of alopecia, e.g., androgenetic alopecia, than would be otherwise expected for a given individual. Efficacy for prevention of alopecia, e.g., androgenetic alopecia, can be established through controlled studies, e.g., in which a subject is administered a treatment (e.g., a topical treatment) and another subject is administered a placebo. Under these circumstances, if the subject treated with the topical treatment undergoes less hair loss over time relative to the subject receiving the placebo, e.g., at least 5% less, at least 10% less, at least 15% less, at least 20% less, at least 25% less, at least 30% less, at least 35% less, at least 40% less, at least 45% less, at least 50% less or beyond, the treatment is effective for the prevention of alopecia, e.g., androgenetic alopecia.

As used herein, the terms "treat," "treatment," or "treating" refer to therapeutic treatments, wherein the object is to reverse, alleviate, ameliorate, inhibit, slow down or stop the progression or severity of a disease or condition, e.g., androgenetic alopecia or other form of alopecia. The term "treating" includes reducing or alleviating at least one adverse effect or symptom of a disease or condition, e.g., androgenetic alopecia or other form of alopecia. Treatment is generally "effective" if one or more symptoms are reduced. Alternatively, treatment is "effective" if the progression of a disease is reduced or halted. That is, "treatment" includes not just the improvement of symptoms, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the extent or amount of hair loss is reduced, or the progression of hair loss is slowed or halted. The term "treatment" of a disease also includes providing relief from the symptoms or side-effects of the disease (including palliative treatment).

As used herein the term "comprising" or "comprises" is used in reference to compositions, methods, etc. refers to component(s) or method steps that are present in the method or composition, yet allows for the composition, method, etc. to also include unspecified elements.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

As used herein the term "alopecia" refers to all forms of hair loss in men and women including but not limited to traction alopecia, androgenetic alopecia, male pattern baldness (MPB), female pattern hair loss (FPHL), alopecia areata, alopecia universalis, telogen effluvium, chemotherapy induced alopecia, hair shedding, eyebrow hair loss, beard hair loss, hair thinning, etc. The term permits the presence of elements that do not materially affect the basic and novel or functional characteristic(s) of that embodiment.

As used herein the term "alkalinizing agent" refers to all agents that either: (i) directly increase the intracellular pH (ii) directly increase the intracellular pH by activating or inhibiting the various ion carriers that regulate cellular pH (iii) upregulate or downregulate the various ion carriers; or (iv) increase the intracellular pH by changing the extracellular pH. The term permits the presence of elements that do not materially affect the basic and novel or functional characteristic(s) of that embodiment.

As used herein the term "acidifying agent" refers to all agents that either: (i) directly decrease the intracellular pH (ii) directly decrease the intracellular pH by activating or inhibiting the various ion carriers that regulate cellular pH (iii) upregulate or downregulate the various ion carriers; or (iv) decrease the intracellular pH by changing the extracellular pH. The term permits the presence of elements that do not materially affect the basic and novel or functional characteristic(s) of that embodiment.

As used herein the term "ion carriers" refers to all cellular ion carriers that either increase or decrease the intracellular pH. In the context of this application ion carriers can be referred to as proton pumps. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Various aspects of the technology described measuring the sulfonating ability of a hair bearing skin, hair follicle, and/or keratinocyte cell. An increase in the sulfonating ability of a hair bearing skin, hair follicle, and/or keratinocyte cell can be interpreted to mean that enzymes or substrates required for this reaction have been increased in concentration, i.e., an increase in substrates will lead to an increase in reaction products (Le Chatelier's principal). For example, increasing the available sulfotranseferase will increase the sulfonating ability of a hair bearing skin, hair follicle, and/or keratinocyte cell. Similarly, increasing the available PAPS or PAPSS (which produces PAPS) will increase the sulfonating ability of a hair bearing skin, hair follicle, and/or keratinocyte cell.

Measurement of the sulfonating ability of a hair bearing skin, hair follicle, and/or keratinocyte cell or a hair follicle can be performed, if necessary, via a colorimetric assay adapted for that purpose. Examples are described in, e.g., Goren A, Shapiro J, Roberts J, McCoy J, Desai N, Zarrab Z, Pietrzak A, Lotti T. Clinical utility and validity of minoxidil response testing in androgenetic alopecia. Dermatol Ther 2015: 28(1): 13-16, which is incorporated herein in its entirety by reference. Briefly, plucked anagen hairs are collected from the scalp and inspected visually for an intact bulb. Suitable hairs are trimmed to a length of ~1 cm and immersed, bulb first, in 100 μL of an assay solution containing 50 mM phosphate buffer (pH8), 5 mM potassium p-nitrophenyl sulfate, 20 μM adenosine 3',5'-diphosphate, 100 μM minoxidil and 5 mM MgCl2. Hairs are allowed to react with the solution for 24 hours at room temperature. After incubation, hairs are removed and the optical absorbance of the solution at 405 nm is determined with a spectrophotometer (e.g., Shimadzu UV-1700, Kyoto, Japan) using a single scan and 1 cm path length.

Increased intracellular pH is necessary for adult epithelial and embryonic stem cell differentiation. Various aspects of the invention describe the increased or decreased rate of hair follicle stem cells (HFSC), rate of differentiation, and/or proliferation. An increase in intracellular pH (pHi) can be used to increase the rate of hair follicle stem cells (HFSC) rate of differentiation and/or proliferation. Similarly, a decrease in intracellular pH (pHi) can be used to decrease the rate of hair follicle stem cells (HFSC) rate of differentiation and/or proliferation. In one aspect of the invention, pHi can be changed by changing the extracellular pH (pHe).

Applicants disclose herein methods to treat or prevent various forms of alopecia, e.g. female pattern hair loss or androgenetic alopecia. The method includes the use of a topical composition applied to the scalp that up-regulates the sulfonating capacity of the hair follicle. The method further includes the use of topical minoxidil applied subsequent to a topical composition applied to the scalp that up-regulates the sulfonating capacity of the hair follicle.

Additionally, applicant discloses herein methods for slowing hair growth. The methods include application of an acidfying agent to the HFSC niche subsequently reducing the HFSC pHi.

In one embodiment, the invention concerns up-regulating the sulfonating capacity of hair bearing skin, hair follicles, and/or keratinocyte cells by applying a topical solution containing an alkalinizing agent that will raise the intracellular pH of cells in the outer root sheath of the hair follicle. Examples of alkalinizing agents include, but are not limited to, sodium bicarbonate, sodium citrate, potassium citrate, calcium carbonate, sodium lactate, and calcium acetate, carbicarb, sodium citrate/citric acid.

In one embodiment, the invention concerns up-regulating the sulfonating capacity of hair bearing skin, hair follicles, and/or keratinocyte cells by applying a topical solution containing an alkalinizing agent that will raise the extracellular pH of cells in the outer root sheath of the hair follicle.

In one embodiment, the invention concerns up-regulating the sulfonating capacity of hair bearing skin, hair follicles, and/or keratinocyte cells by applying a topical solution containing an alkalinizing agent with a penetration enhancer. Examples of penetration enhancers include, but are not limited to, alcohols, glycols (e.g., diethylene glycol and tetraethylene glycol), fatty acids (e.g., lauric acid, myristic acid and capric acid), fatty esters, fatty ethers, cyclodextrines, occlusive agents, surface active agents, dimethylaminopropionic acid derivatives, terpenes, sulfoxides, cyclic ethers, amides, and amines. Other examples of penetration enhancers can include sulphoxides (such as dimethylsulphoxide, DMSO, decylmethalsulfoxide), Azones (e.g., 1-dodecylazacycloheptan-2-one, laurocapran, or laurocapram), pyrrolidones (e.g., 2-pyrrolidone, 2P, N-methylpyrrilidone, N-methyl-2-pyrrolidone, NMP, 1-propyl-3-dodecyl-2-pyrrolidone, 1-butyl-3-dodecyl-2-pyrrolidone), alcohols and alkanols (ethanol, or decanol), glycols (e.g., propylene glycol), surfactants (e.g., polyoxyethylene-2-oleyl ether, polyoxy ethylene-2-stearly ether, sodium dodecyl sulfate, SDS, sodium lauryl sulfate, SLS), Oxazolidinones (e.g., 4-decyloxazolidin-2-one), urea, 2-(1-nonyl)-1,3-dioxolane, and terpenes. Additional examples of penetration enhancers can include polyester nanosponges, liposomes, phospholipids, cyclopentadecalactone, pentadecalactone, SNAC, salcaprozate sodium Sodium N-[8-(2-hydroxybenzoyl) amino] caprylate, CNAC, 5-CNAC, 8-(N-2-hydroxy-5-chloro-benzyl)-amino-caprylic acid, sodium caprate, glyceryl triglyceride, and peptides.

In one embodiment, the invention concerns up-regulating the sulfonating capacity of hair bearing skin, hair follicles, and/or keratinocyte cells by applying a topical solution containing an alkalinizing agent with a device designed to increase transdermal penetration. Examples of devices designed to increase transdermal penetration include micro-needle arrays and iontophoretic patches.

In one embodiment, the invention concerns up-regulating the sulfonating capacity of hair bearing skin, hair follicles, and/or keratinocyte cells by raising the intracellular pH of stem cells in the outer root sheath of a hair follicle. In one embodiment, intracellular pH of stem cells may be alkalinized by application of a topical proton pump agonist. In another embodiment, intracellular pH of stem cells may be alkalinized by application of a topical proton pump agonist.

In one embodiment, the invention concerns treatment of alopecia by inducing HFSC differentiation and hair anagen cycle elongation by applying a topical solution containing an alkalinizing agent that will raise the extracellular pH of cells in the outer root sheath of the hair follicle.

In one embodiment, the invention concerns treatment of alopecia by inducing HFSC differentiation and hair anagen cycle elongation by applying a topical solution containing an alkalinizing agent with a penetration enhancer. Examples of penetration enhancers include, but are not limited to, alcohols, glycols (e.g., diethylene glycol and tetraethylene glycol), fatty acids (e.g., lauric acid, myristic acid and capric acid), fatty esters, fatty ethers, cyclodextrines, occlusive agents, surface active agents, dimethylaminopropionic acid derivatives, terpenes, sulfoxides, cyclic ethers, amides, and amines. Other examples of penetration enhancers can include sulphoxides (such as dimethylsulphoxide, DMSO, decylmethalsulfoxide), Azones (e.g., 1-dodecylazacycloheptan-2-one, laurocapran, or laurocapram), pyrrolidones (e.g., 2-pyrrolidone, 2P, N-methylpyrrilidone, N-methyl-2-pyrrolidone, NMP, 1-propyl-3-dodecyl-2-pyrrolidone, 1-butyl-3-dodecyl-2-pyrrolidone), alcohols and alkanols (ethanol, or decanol), glycols (e.g., propylene glycol), surfactants (e.g., polyoxyethylene-2-oleyl ether, polyoxy ethylene-2-stearly ether, sodium dodecyl sulfate, SDS, sodium lauryl sulfate, SLS), Oxazolidinones (e.g., 4-decyloxazolidin-2-one), urea, 2-(1-nonyl)-1,3-dioxolane, and terpenes. Additional examples of penetration enhancers can include polyester nanosponges, liposomes, phospholipids, cyclopentadecalactone, pentadecalactone, SNAC, salcaprozate sodium Sodium N-[8-(2-hydroxybenzoyl) amino]caprylate, CNAC, 5-CNAC, 8-(N-2-hydroxy-5-chloro-benzyl)-aminocaprylic acid, sodium caprate, glyceryl triglyceride, and peptides.

In one embodiment, the invention concerns treatment of alopecia by inducing HFSC differentiation and hair anagen cycle elongation by applying a topical solution containing an alkalinizing agent with a device designed to increase transdermal penetration. Examples of devices designed to increase transdermal penetration include micro-needle arrays and iontophoretic patches.

In one embodiment, the invention concerns increasing hair graft survival and reducing shock hair loss post hair surgery by applying a topical solution containing an alkalinizing agent that will raise the extracellular pH of cells in the outer root sheath of the hair follicle. The application of the topical solution can be made by a sprayer or mist.

In one embodiment, the invention concerns increasing hair graft survival and reducing shock hair loss post hair surgery by applying a topical solution containing an alkalinizing agent with a penetration enhancer. Examples of penetration enhancers include, but are not limited to, alcohols, glycols (e.g., diethylene glycol and tetraethylene glycol), fatty acids (e.g., lauric acid, myristic acid and capric acid), fatty esters, fatty ethers, cyclodextrines, occlusive agents, surface active agents, dimethylaminopropionic acid derivatives, terpenes, sulfoxides, cyclic ethers, amides, and amines. Other examples of penetration enhancers can include sulphoxides (such as dimethyl sulphoxide, DMSO, decylmethalsulfoxide), Azones (e.g., 1-dodecyl azacycloheptan-2-one, laurocapran, or laurocapram), pyrrolidones (e.g., 2-pyrrolidone, 2P, N-methylpyrrilidone, N-methyl-2-pyrrolidone, NMP, 1-propyl-3-dodecyl-2-pyrrolidone, 1-butyl-3-dodecyl-2-pyrrolidone), alcohols and alkanols (ethanol, or decanol), glycols (e.g., propylene glycol), surfactants (e.g., polyoxyethylene-2-oleyl ether, polyoxy ethylene-2-stearly ether, sodium dodecyl sulfate, SDS, sodium lauryl sulfate, SLS), Oxazolidinones (e.g., 4-decyloxazolidin-2-one), urea, 2-(1-nonyl)-1,3-dioxolane, and terpenes. Additional examples of penetration enhancers can include polyester nanosponges, liposomes, phospholipids, cyclopentadecalactone, pentadecalactone, SNAC, salcaprozate sodium Sodium N-[8-(2-hydroxybenzoyl) amino]caprylate, CNAC, 5-CNAC, 8-(N-2-hydroxy-5-chloro-benzyl)-aminocaprylic acid, sodium caprate, glyceryl triglyceride, and peptides.

In one embodiment, the invention concerns increasing hair graft survival and reducing shock hair loss post hair surgery by applying a topical solution containing an alkalinizing agent with a device designed to increase transdermal penetration. Examples of devices designed to increase transdermal penetration include micro-needle arrays and iontophoretic patches.

In one embodiment, the invention concerns reducing hair or the rate of growth of hair on hair bearing skin, hair follicles, and/or keratinocyte cells by applying a topical solution containing an acidifying agent that will lower the intracellular pH of cells in the outer root sheath of the hair follicle. Examples of acidifying agents include, but are not limited to, citric acid, ascorbic acid, vitamin C, lactic acid, acetic acid, etc.

In one embodiment, the invention concerns reducing hair or the rate of growth of hair on hair bearing skin, hair follicles, and/or keratinocyte cells by applying a topical solution containing an acidifying agent and a penetration enhancer.

In one embodiment, the invention concerns up-regulating the sulfonating capacity of hair bearing skin, hair follicles, and/or keratinocyte cells by applying a topical solution containing an agonist of the AhR nuclear receptor. Examples of AhR agonists include, but are not limited to, PAHs, TCDD (other PHAHs), β-naphthoflavone, indigoids, tryptophan metabolites, omeprazole, and lansoprazole.

In one embodiment, the invention concerns up-regulating the sulfonating capacity of hair bearing skin, hair follicles, and/or keratinocyte cells by applying a topical solution containing an agonist of the CAR nuclear receptor. Examples of CAR agonists include, but are not limited to, phenobarbital, phenytoin, carbamazepine, CITCO (human), TCPOBOP (mouse), clotrimazole, Yin Zhi Wuang (many PXR agonists are also CAR agonists, and vice versa), and meclizine.

In one embodiment, the invention concerns up-regulating the sulfonating capacity of hair bearing skin, hair follicles, and/or keratinocyte cells by applying a topical solution containing an agonist of the PXR nuclear receptor. Examples of PXR agonists include, but are not limited to, amprenavir, avasimibe, bosentan, bile acids, carbamazepine, clindamycin, clotrimazole, cortisol, cyproterone acetate, dicloxacillin, efavirenz, etoposide, dexamethasone, genistein, griseofulvin, guggulsterone, guttiferone G, garcinol, Isogarcinol hyperforin (Saint John's Wort), indinavir, lovastatin, mifepristone, nafcillin, nelfinavir, nifedipine, omeprazole, paclitaxel, PCBs, phenobarbital, phthalate monoesters, 5β-pregnane-3,20-dione, rifabutin, rifampin, ritonavir, saquinavir, simvastatin, spironolactone, sulfinpyrazole, TAO, tetracycline, topotecan, transnanoclor, troglitazone, verapamil, vitamin E, vitamin K2, artemisinin, PCN, LCA, cafestol, SR-12813, rifaximin, mevastatin, TO901317, Solomonsterol A, and meclizine.

In one embodiment, the invention concerns up-regulating the sulfonating capacity of hair bearing skin, hair follicles, and/or keratinocyte cells by applying a topical solution containing an agonist of the PPARα nuclear receptor. In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agonist of the PPARα nuclear receptor. Examples of PPARα agonists include, but are not limited to, fibrates, WY-14,643, and perfluorodecanoic acid.

In one embodiment, the invention concerns up-regulating the sulfonating capacity of hair bearing skin, hair follicles, and/or keratinocyte cells by applying a topical solution containing an agonist of the Nrf2 nuclear receptor. In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agonist of the Nrf2 nuclear receptor. Examples of Nrf2 agonists include, but are not limited to, β-Naphthoflavone, oltipraz, phenolic antioxidants (e.g., BHA and BHT) and various glutathione depletors.

In one embodiment, the invention concerns up-regulating the sulfonating capacity of hair bearing skin, hair follicles, and/or keratinocyte cells by applying a composition comprising an activator of the Nrf2 (Nuclear factor erythroid 2-related factor 2) nuclear factor to a hair follicle cell and/or a keratinocyte cell. Examples of Nrf2 activators include, but are not limited to, Sulforaphane, Resveratrol, Curcumin, Quercetin, Epigallocatechin-3-gallate, Diallyl sulfide, Naringenin, Pterostilbene, Caffeic Acid Phenethyl Ester, Fisetin, Lithospermate B, Ferulic acid, Zerumbone, Carnosol, Cafestol, Ellagic acid, Eugenol, Kaempferol, β-Naphthoflavone, oltipraz, Bardoxolone methyl, RTA 408, CDDO-Im, Bardoxolone, Danshensu, CDDO-EA, Mangiferin, Acetylcysteine, also known as N-acetylcysteine (NAC), butylated hydroxytoululene, BHA (butylated hydroxyanisole), BHT (butylated hydroxytoluene), phenolic antioxidants (e.g., BHA and BHT) and various glutathione depletors.

In one embodiment, the invention concerns up-regulating the sulfonating capacity of hair bearing skin, hair follicles, and/or keratinocyte cells by applying a composition comprising an inducer of the Nrf2 nuclear factor (encoded by the NFE2L2 gene) to a hair follicle cell and/or a keratinocyte cell, i.e., agents that increase the transcription of NFE2L2. Examples of inducers are 4-Hydroxyphenylacetic acid and acetylation via p300/CBP.

In one embodiment, the invention concerns up-regulating the sulfonating capacity of hair bearing skin, hair follicles, and/or keratinocyte cells by applying a composition comprising an agent that disassociates Nrf2 from Keap 1 (Kelch-like ECH-associated protein 1) to a hair follicle cell and/or a keratinocyte cell. The agent can be selected to disassociate Nrf2 from Keap1 by alkylation of Keap 1, or some other process. Keap 1, a repressor protein, binds to Nrf2 and promotes its degradation by the ubiquitin proteasome pathway. Keap 1 binding and subsequent promotion of the ubiquitination is the major regulatory mechanism for Nrf2 controlled genes. An example of such an agent is 4-Octyl Itaconate.

In one embodiment, the invention concerns up-regulating the sulfonating capacity of hair bearing skin, hair follicles, and/or keratinocyte cells by applying a composition comprising a direct or indirect inhibitor of Keap1 (either a protein inhibitor (e.g., competitive/non-competitive inhibiter of Nrf2 binding) or an agent that reduces the transcription expression of Keap 1 mRNA) to a hair follicle cell and/or a keratinocyte cell. Examples of direct inhibitors are mir-200a, RTA 408, and LH601A.

In one embodiment, the invention concerns up-regulating the sulfonating capacity of hair bearing skin, hair follicles, and/or keratinocyte cells by applying a composition comprising an agent that down-regulates Keap 1 (Keap 1 gene) expression to a hair follicle cell and/or a keratinocyte cell.

In one embodiment, the invention concerns up-regulating the sulfonating capacity of hair bearing skin, hair follicles, and/or keratinocyte cells by applying a composition comprising an inducer of the activity of or an agent that increases the activity of p300/CBP to a hair follicle cell and/or a keratinocyte cell. Examples of such agents are agents that increase intracellular pH. This can involve increasing intercellular pH to an alkaline pH range of 7.4-11.0.

In one embodiment, the invention concerns up-regulating the sulfonating capacity of hair bearing skin, hair follicles, and/or keratinocyte cells by applying a composition comprising an agent that increases the state of oxidative stress of a cell, wherein the composition is applied to a hair follicle cell and/or a keratinocyte cell. Examples of oxidative stress inducers are agents that increase intracellular pH (alkaline pH range 7.4-11.0), such an alkaline solution containing a buffer, e.g., bicarbonate (e.g., sodium bicarbonate).

In one embodiment, the invention concerns a kit having any of the compositions and/or therapeutic agents disclosed herein configured to up-upregulate the sulfonating capacity of hair bearing skin, hair follicles, and/or keratinocyte cells. The kit comprises a dispenser, implant, or pill. The composition and/or therapeutic agent is mixed with minoxidil or is packaged in the dispenser, implant, or pill with minoxidil.

In one embodiment, the invention concerns a kit having any of the compositions and/or therapeutic agents disclosed herein configured to up-upregulate the sulfonating capacity of hair bearing skin, hair follicles, and/or keratinocyte cells. The kit comprises a first dispenser, first implant, or first pill. The kit comprises a second dispenser, second implant, or second pill. The composition and/or therapeutic agent is packaged in the first dispenser, first implant, or first pill. The minoxidil is packaged in the second dispenser, second implant, or second pill.

In one embodiment, the invention concerns up-regulating the sulfonating capacity of hair bearing skin, hair follicles, and/or keratinocyte cells by applying a topical solution containing an agonist of the GR nuclear receptor. In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agonist of the GR nuclear receptor. Examples of GR agonists include, but are not limited to, glucocorticoids.

In one embodiment, the invention concerns up-regulating the sulfonating capacity of hair bearing skin, hair follicles, and/or keratinocyte cells by applying a topical solution containing an agonist of the FXR nuclear receptor. In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agonist of the FXR nuclear receptor. Examples of FXR agonists include, but are not limited to, bile acids, GW4064, AGN29, AGN31, cafestol, fexaramine, XL335, WAY-362450, FXR-450, obeticholic acid (OCA), PX 20350, and DY 268.

In one embodiment, the invention concerns up-regulating the sulfonating capacity of hair bearing skin, hair follicles, and/or keratinocyte cells by applying a topical solution containing an agonist of the LXRα nuclear receptor. In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agonist of the LXRα nuclear receptor. Examples of LXRα agonists include, but are not limited to, GW3965, T0901317, paxiline, F3methylAA, and acetylpodocarpic dimer (APD).

In one embodiment, the invention concerns up-regulating the sulfonating capacity of hair bearing skin, hair follicles, and/or keratinocyte cells by applying a topical solution containing an agonist of the VDR nuclear receptor. In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agonist of the VDR nuclear receptor. Examples of VDR agonists include, but are not limited to, 1α,25-Dihydroxyvitamin D3 and lithocholate.

In one embodiment, the invention concerns up-regulating CYP1A1, 1A2, 1B1, 2S1, UGT1A1, or UGT1A6 in hair bearing skin, hair follicles, and/or keratinocyte cells by applying a topical solution containing an agonist of the AhR nuclear receptor. In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agent that up-regulates CYP1A1, 1A2, 1B1,2S1, UGT1A1, or UGT1A6. The topical solution containing an agonist of the AhR nuclear receptor. Examples of AhR agonists include, but are not limited to, PAHs, TCDD (other PHAHs), 3-naphthoflavone, indigoids, tryptophan metabolites, omeprazole, and lansoprazole.

In one embodiment, the invention concerns up-regulating CYP2A6, 2B6, 2C8, 2C9, 2C19, 3A4, UGT1A1, SULT1A1, ALAS, MRP2, or MRP3 concentration in hair bearing skin, hair follicles, and/or keratinocyte cells by applying a topical solution containing an agonist of the CAR nuclear receptor. In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agonist of the CAR nuclear receptor. Examples of CAR agonists include, but are not limited to, phenobarbital, phenytoin, carbamazepine, CITCO (human), TCPOBOP (mouse), clotrimazole, and Yin Zhi Wuang (many PXR agonists are also CAR agonists, and vice versa).

In one embodiment, the invention concerns up-regulating CYP2B6, 2C8, 2C9, 2C19, 3A4, 3A7, 7A1, SULT2A1, UGT1A1, 1A3, 1A4, PAPSS2, ALAS, MDR1, or AhR concentration in hair bearing skin, hair follicles, and/or keratinocyte cells by applying a topical solution containing an agonist of the PXR nuclear receptor. In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agonist of the PXR nuclear receptor. Examples of PXR agonists include, but are not limited to, amprenavir, avasimibe, bosentan, bile acids, carbamazepine, clindamycin, clotrimazole, cortisol, cyproterone acetate, dicloxacillin, efavirenz, etoposide, dexamethasone, genistein, griseofulvin, guggulsterone, guttiferone G, garcinol, Isogarcinol hyperforin (Saint John's Wort), indinavir, lovastatin, mifepristone, nafcillin, nelfinavir, nifedipine, omeprazole, paclitaxel, PCBs, phenobarbital, phthalate monoesters, 5β-pregnane-3,20-dione, rifabutin, rifampin, ritonavir, saquinavir, simvastatin, spironolactone, sulfinpyrazole, TAO, tetracycline, topotecan, transnanoclor, troglitazone, verapamil, vitamin E, vitamin K2, artemisinin, PCN, LCA, cafestol, SR-12813, rifaximin, mevastatin, TO901317, Solomonsterol A, and meclizine.

In one embodiment, the invention concerns up-regulating BSEP, I-BABP, MDR3, UGT2B4, SULT2A1, OATP8, PPARa, or SHP concentration in hair bearing skin, hair follicles, and/or keratinocyte cells by applying a topical solution containing an agonist of the FXR nuclear receptor. Examples of FXR agonists include, but are not limited to, bile acids, GW4064, AGN29, and AGN31.

In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agonist of the RXR nuclear receptor. Examples of RXR agonists include but are not limited to 9-cis-retinoic acid, all trans retinoic acid, ATRA, retinol (or retinal or retinaldehyde), retin-A, (E)-5,8,11,14,17,20-docosahexaenoic acid, lithocholic acid, phytanic acid, 9cUAB30, AGN194204, CD3254L, G100268, LG101305, methoprene acid, PA024, SR11217, SR11237 (BMS649), DEC1, DR5III, PRIC295, bexarotene, CD3254, decosahexaenoic, flurobexarotene, LG 100268, LG 100754, isotretinoin, etc.

In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agonist of the RAR nuclear receptor. Examples of RAR agonists include but are not limited to all-trans-retinoic acid, ATRA, retinol (or retinal or retinaldehyde), retin-A, 9-cis-retinoic acid, all-trans-5,6-epoxy retinoic acid, DR5III, isotretinoin, AC 261066, AC 55649, adapalene, AM 580, AM 80, BMS 753, BMS 961, BMS 453, CD 1530, CD 2314, CD 437, Ch 55, tazarotene, TTNPB, AR-7, FOXO1, SMRT, N-CoR, SMRTER, EC 19, etc.

In one embodiment, the invention concerns up-regulating the sulfonating capacity of hair bearing skin, hair follicles, and/or keratinocyte cells by applying a topical solution containing an alkalinizing agent or an alkalinizing agent with a penetration enhancer with an agonist of the FXR nuclear receptor. Examples of FXR agonists include, but are not limited to, bile acids, GW4064, AGN29, and AGN31.

In one embodiment, the invention concerns increasing the activity of sulfotransferase by generating an embodiment of the composition disclosed herein and incorporating the composition into a solution. The method can further include adjusting the pH of the solution to be greater than 7. The method can involve applying the solution with the composition to skin of a person. Having a solution with an embodiment of the composition, wherein the solution has a pH greater than 7 can increase the activity of sulfotransferase, which can include increasing the SULT1A1 enzyme metabolic activity.

Nuclear receptor agonists may be administered to the hair follicle or scalp to increase the sulfonating capacity of hair bearing skin, hair follicles, and/or keratinocyte cells, treat or prevent alopecia and the other disorders discussed herein. It is specifically contemplated that a nuclear receptor agonists known in the art or disclosed herein can be administered to the hair follicle or the scalp in combination with an agent that retards systemic absorption of the agent across the dermis. In this manner, agents that might otherwise have unwanted systemic effects can be used to treat, reduce or prevent alopecia or other disorders discussed herein while avoiding such systemic side effects. One formulation of agents for topical administration in a manner that avoids systemic absorption is discussed in detail in U.S. 2009/0068287, which is incorporated herein by reference in its entirety.

In one aspect, the therapeutic agent, such as the nuclear receptor agonist or an alkalinizing agent or an alkalinizing agent with a penetration enhancer, is applied to a skin section, such as a section of the scalp, that contains at least one hair follicle.

In one aspect of the present invention, a kit for measuring the pH of a subject's hair follicle is used to diagnose androgenetic alopecia. In one aspect of the present invention a kit for measuring the pH of a subject's hair follicle is used to diagnose minoxidil response. In another aspect a kit for measuring the pH of a subject's hair follicle is used to detect stem cell proliferation in a hair follicle. In yet another embodiment the efficacy of a hair growing treatment is assessed by measuring the pH of a subject's hair follicle at baseline with a kit for measuring the pH of a subject's hair follicle, using a hair growing treatment for a prescribed time, and finally measuring the pH of a subject's hair follicle after using the treatment for comparison to baseline.

In one aspect of the present invention, a kit for measuring the pH of a subject's hair follicle is used. The kit comprising Bromothymol Blue (0.04%) and a 20× magnification stereo microscope equipped with a 5MP Color Digital Eyepiece Microscope Camera.

In one embodiment of the present invention intracellular alkalization is achieved by activating one or more ion channels that regulate cytoplasm pH such as but not limited to: $Na^+$—$H^+$ exchangers (NHEs), $Na^+$—$HCO_3^-$ co-transporters (NBCs), $Na^+$-DEPENDENT $CL^-$- $HCO_3^-$ exchangers (NDCBEs), $Na^+$—$K^+$-ATPase pumps (NKAs). Activating the ion channels that result in intracellular alkalization can be made by using one or more of the following agents: saxitoxin, neosaxitoxin, tetrodotoxin, oxcarbazepine, carbamazepine, quinidine, procainamide, disopyramide, lidocaine, mexiletine, tocainide, phenytoin, encainide, flecainide, moricizine, propafenone, aconitine, batrachotoxin, robustoxin, versutoxin, ciguatoxins, DDT, pyrethrines, fenvalerate, solnatide (AP301), ambroxol, bromhexine, articaine hydrochloride, articaine, benzamil, bupivacaine, camostat mesylate, carbamazepine, cariporide, 3',4'-dichlorobenzamil, disopyramide, encainide, flecainide acetate, GMQ, halofantrine, lappaconitine, levobupivacaine, lidocaine, lidocaine hydrochloride, lidocaine N-ethyl chloride, lorcainide, metolazone, mexiletine, ouabain octahydrate, PF-01247324, PF-04531083, PF-04856264, PF-05089771, PF-06305591, pilsicainide, a-pompilidotoxin, procaine, propafenone, ProTx-II, pyrethrum, quinidine, quinidine sulfate, ralfinamide, ralfinamide mesylate, rostafuroxin, safinamide, safinamide mesylate, tocainide, tolperisone, UCL 2077, veratridine, zoniporide, etc.

In one embodiment of the present invention, intracellular alkalization is achieved by up-regulating one or more ion channels that regulate cytoplasm pH such as but not limited to: $Na^+$—$H^+$ exchangers (NHEs), $Na^+$— $HCO_3^-$ co-transporters (NBCs), Ne-dependent $Cl^-$—$HCO_3^-$ exchangers (NDCBEs), $Na^+$—$K_+$-ATPase pumps (NKAs). Up-regulating the ion channels that result in intracellular alkalization can be made by using one or more of the following agents: angiotensin II, catecholamines, endothelin-1, glucocorticoids, NPY, thyroid hormones, etc.

In one embodiment of the present invention, intracellular alkalization is achieved by inhibiting one or more ion channels that regulate cytoplasm pH such as but not limited to: $Cl^-$—$HCO_3^-$ or anion exchangers (AEs), $Ca^{2+}$-ATPases (PMCAs). Inhibiting the ion channels that result in intracellular alkalization can be made by using one or more of the following agents: cholestyramine, colestipol, colesevelam, rifampicin, naltrexone, naloxone, sertraline, EIPA, acetazolamide, amlodipine (Norvasc), aranidipine (Sapresta), azelnidipine (Calblock), barnidipine (HypoCa), benidipine (Coniel), cilnidipine (Atelec, Cinalong, Siscard), clevidipine (Cleviprex), efonidipine (Landel), felodipine (Plendil), isradipine (DynaCirc, Prescal), lacidipine (Motens, Lacipil), lercanidipine (Zanidip), manidipine (Calslot, Madipine), nicardipine (Cardene, Carden S R), nifedipine (Procardia, Adalat), nilvadipine (Nivadil), nimodipine (Nimotop), nisoldipine (Baymycard, Sular, Syscor), nitrendipine (Cardif, Nitrepin, Baylotensin), pranidipine (Acalas), fendiline, gallopamil, verapamil (Calan, Isoptin), diltiazem (Cardizem), mibefradil, bepridil, flunarizine, fluspirilene, fendiline, gabapentinoids, gabapentin, pregabalin, ziconotide, niflumic acid, anthracene-9-carboxylic acid, etc.

In one embodiment of the present invention, intracellular alkalization is achieved by down-regulating one or more ion channels that regulate cytoplasm pH such as but not limited to: $Cl^-$— $HCO_3^-$ or anion exchangers (AEs), $Ca^{2+}$-ATPases (PMCAs). Down-regulating the ion channels that result in intracellular alkalization can be made by using one or more of the following agents: angiotensin II, catecholamines, endothelin-1, glucocorticoids, NPY, thyroid hormones, etc.

In one embodiment of the present invention, intracellular acidification is achieved by activating one or more ion channels that regulate cytoplasm pH such as but not limited to: $Cl^-$—$HCO_3^-$ or anion exchangers (AEs), $Ca^{2+}$-ATPases (PMCAs). Activating the ion channels that result in intracellular acidification can be made by using one or more of the following agents: Bay K8644, nifedipine, ambroxol, lubiprostone, Amitiza (Pro), 1,10-phenanthroline, or GABA-A receptor agonists (e.g lorazepam), etc.

In one embodiment of the present invention, intracellular acidification is achieved by up-regulating one or more ion channels that regulate cytoplasm pH such as but not limited to: $Cl^-$—$HCO_3^-$ or anion exchangers (AEs), $Ca^{2+}$-ATPases (PMCAs). Up-regulating the ion channels that result in intracellular acidification can be made by using one or more of the following agents: angiotensin II, catecholamines, endothelin-1, glucocorticoids, NPY, thyroid hormones, etc.

In one embodiment of the present invention, intracellular acidification is achieved by inhibiting one or more ion channels that regulate cytoplasm pH such as but not limited to: $Na^+$—$H^+$ exchangers (NHEs), $Na^+$—$HCO_3^-$ co-transporters (NBCs), $Na^+$-dependent $Cl^-$—$HCO_3^-$ exchangers (NDCBEs), $Na^+$—$K^+$-ATPase pumps (NKAs). Inhibiting the ion channels that result in intracellular acidification can be made by using one or more of the following agents: S—(N-ethyl-N-isopropyl) amiloride, zoniporide, cariporide, KR-32568 [5-(2-Methyl-5-fluorophenyl)furan-2-ylcarbonyl]guanidine, eniporide, EMD87580 [(2-methyl-4,5-di-(methyl sulfonyl)-benzoyl)-guanidine], HMA [5-(N,N-hexamethylene)-amiloride], KR-33028 (4-cyano (benzo[b]thiophene-2-carbonyl)guanidine), S0859, [2-chloro-N-[[2'-[(cyanoamino)sulfonyl][1,1'-biphenyl]-4-yl]methyl]-N-[(4-methylphenyl)methyl]-benzamide, levetiracetam, hydrochlorothiazide (HCTZ), ouabain, dihydroouabain, lanatoside C, bufalin, digitoxin, digoxin, strophantidin, ouabagenin, etc.

In one embodiment of the present invention, intracellular acidification is achieved by down-regulating one or more ion channels that regulate cytoplasm pH such as but not limited to: $Na^+$—$H^+$ exchangers (NHEs), $Na^+$—$HCO_3^-$ co-transporters (NBCs), $Na^+$-dependent $Cl^-$—$HCO_3^-$ exchangers (NDCBEs), $Na^+$—$K^+$-ATPase pumps (NKAs). Down-regulating the ion channels that result in intracellular acidification can be made by using one or more of the following agents: angiotensin II, catecholamines, endothelin-1, glucocorticoids, NPY, thyroid hormones, etc.

In one embodiment of the present invention, intracellular alkalization or acidification is achieved by activating endogenous pH sensors such as but not limited to acid-sensing ion channels, pH-sensing ionotropic receptors, pH-sensing metabotropic receptors, transient receptor potential ion channels, TRPV1, TRPC4, TRPC5, TRPP2, and purinoceptors, etc.

Formulations

The therapeutic agents, particularly the nuclear receptor agonists and/or the alkalinizing agents, described herein and used in the present methods may be formulated into compositions according to the knowledge of one of skill in the art. In one embodiment, the nuclear receptor agonist and/or the alkalinizing agent or other inducer of sulfotransferase is formulated for topical slow or prolonged release. As but one example, in one embodiment the inducer of sulfotransferase is encapsulated for slow release.

The therapeutic agents, particularly the nuclear receptor agonists and/or the alkalinizing agent, described herein and used in the present methods may be formulated into compositions according to the knowledge of one of skill in the art. In one embodiment, the nuclear receptor agonist or other inducer of sulfotransferase is encapsulated in order to increase the water solubility of the therapeutic agent. In another embodiment, the nuclear receptor agonist or other inducer of sulfotransferase is encapsulated in order to reduce the loss through degradation of therapeutic agent, for example, to reduce oxidation of the therapeutic agent.

In one embodiment hyperforin is encapsulated to overcome its poor water solubility and facile oxidative degradation.

In one embodiment of the present invention a diagnostic test is used to determine if a subject will likely have sulfotransferase up-regulated by a particular PXR agonist. For example, a genetic test of the PXR gene may identify if human PXR was rendered hyperforin insensitive via mutagenesis of Leu308 to phenylalanine. Other methods are possible.

In one embodiment of the present invention a PXR agonist, CAR agonist, an alkalinizing agent, and/or acidifying agent is secreted from a genetically modified organism (GMO) that is transplanted to the human skin.

In one embodiment of the present invention a PXR agonist, CAR agonist, and/or an alkalinizing agent is secreted from a bacterial organism that is applied as a pro-biotic to the human skin In one embodiment of the present invention the use of a topical composition applied to the scalp that up-regulates the sulfonating capacity of the hair follicle is used to increase the efficacy of a low-dose oral minoxidil. The method further includes the use of topical composition applied to the scalp that up-regulates the sulfonating capacity of the hair follicle to target minoxidil activation to the scalp for a subject receiving oral, low-dose minoxidil. Examples of oral low-dose minoxidil include dosage less than 0.5 mg once daily. Other examples include 0.45 mg, 0.4 mg, 0.35 mg, 0.30 mg, 0.25 mg, 0.20 mg, 0.15 mg, 0.10 mg, 0.05 mg, 250 µM, 10 µM, used once daily.

In another embodiment, the nuclear receptor agonist or other inducer of sulfotransferase or PAPS is formulated in a shampoo, a foam, ointment, spray, solution, gel, slow release capsule, oral tablet, dry shampoo, or any similar compound or delivery vehicle or methodology. Topical application is preferred. In one embodiment, the composition is formulated in a topical cream. In another embodiment, the composition is formulated in a hair styling product selected from the group consisting of a styling gel, a styling foam, and a hair conditioner.

In another embodiment, the composition may comprise an exfoliating agent to promote abrasion of the surface of the scalp. Examples of the exfoliating agent include (1) inorganic and/or metallic particles such as: boron nitride, in body-centered cubic form (Borazon); aluminosilicate (e.g. nepheline); zircon; mixed oxides of aluminum such as emery; zinc oxide; aluminum oxides such as aluminas or corundum; titanium oxide; titanium oxide coated mica; carbides, in particular silicon carbide (carborundum); or other metal oxides; metals, and metal alloys such as iron shot, steel shot, and in particular perlite; silicates such as glass, quartz, sand, or vermiculite; calcium carbonate (e.g. Bora-Bora sand or Rose de Brignoles sand) or magnesium carbonate; sodium chloride; pumice stone; amorphous silica; diamond; ceramics, and (2) organic particles such as: fruit stones, in particular apricot stones, e.g. Scrubami® apricot; wood cellulose, e.g. ground bamboo stem; coconut shell, e.g. coconut exfoliator; polyamides, in particular Nylon-6; sugars; plastic microbeads, e.g. polyethylenes or polypropylenes; ground walnut; ground apricot seed; ground shells, and (3) mixed particles associating organic and inorganic compounds, and particles coated in the above compounds. The exfoliating agents may be in the form of microbeads of less than five millimeters in its largest dimension that have an exfoliating effect.

In another embodiment, the composition may comprise an exfoliating agent to promote absorption of the nuclear receptor agonist and/or the alkalinizing agent into scalp. An example of the exfoliating agent include salicylic acid.

In one embodiment, the composition comprising a nuclear receptor agonist and/or the alkalinizing agent can be formulated as a drug (which may include a drug with minoxidil). In one embodiment, the composition comprising a nuclear receptor agonist and/or an alkalinizing agent can be formulated as a cosmetic product. In one embodiment, the composition comprising a nuclear receptor agonist and/or the alkalinizing agent can be formulated as a cosmetic product to be used before using minoxodil.

The amount of therapeutic agent present in the composition may be determined by one of skill in the art using known methodologies. In certain embodiments, the nuclear receptor agonist and/or the alkalinizing agent or other inducer of sulfotransferase or PAPS is present in the composition in a concentration from about 0.0020% to 0.0030%, or about 0.0025% by weight. In another embodiment, the therapeutic agent such as a nuclear receptor agonist and/or an alkalinizing agent is present in the composition in a concentration of about 0.0025%, 0.0033%, 0.005%, 0.01%, 0.02%, 0.025%, or 0.10% by weight.

In other embodiments, the therapeutic agent, such as the nuclear receptor agonist and/or the alkalinizing agent, is present in the topical composition for use in the methods disclosed herein in a concentration from about 0.1% to 35%, about 1.0% to 30%, about 0.2% to 30%, about 0.2% to 25%, about 0.2% to 20%, about 0.2% to 15%, about 0.2% to 10%, about 0.2% to 5%, about 0.2% to 4%, about 0.2% to 3%, about 0.2% to 2%, about 0.2% to 1%, about 10.0% to 30%, about 15.0% to 30%, about 20.0% to 30%, about 10% to 20%, about 10% to 15%, about 15% to 20%, about 15% to 60%, about 20% to 60%, about 50% to 60%, and about 45% to 55% by weight.

In one embodiment, the composition comprises a nuclear receptor agonist and/or an alkalinizing agent in a concentration of about 0.025%, about 0.033%, about 0.05%, about 0.1%, about 0.2%, about 0.25%, about 0.30%, about 0.40%, about 1.0%, about 1.5%, about 2.0%, or about 2.5% by weight.

The compositions used in the present disclosure, particularly compositions containing a nuclear receptor agonist and/or an alkalinizing agent, may be formulated with a preservative such as EDTA (0.1-0.5% by weight of the formulation) and/or sodium metabisulfite (0.1-0.5% by weight of the formulation). In some embodiments, the penetration enhancer is selected from one or more of the group consisting of alcohols, glycols, fatty acids, fatty esters, fatty ethers, occlusive agents, surface active agents, dimethylaminopropionic acid derivatives, terpenes, sulfoxides, cyclic ethers, amides, and amines. Other components of the formulations used herein may be chosen from cosmetically approved excipients known in the art, including water, thickeners, etc.

The composition may be packaged in a kit with an applicator for application to the skin. The invention is also directed to a kit comprising a composition of the therapeutic agent, such as a nuclear receptor agonist, and an applicator, and to a kit comprising a composition of the therapeutic agent, such as a nuclear receptor agonist, and a hair brush or comb, particularly a brush or comb that provides exfoliating effect on the scalp such that there is light abrasion after its use that enhances penetration of the therapeutic agent to the AP muscle and/or hair follicle. In one embodiment, the therapeutic agent is provided in a metered dose applicator that provides for a fixed volume of the composition to be administered with each administration, such as 1 ml of the topical composition per administration.

The composition may be packaged in a kit including a topical minoxidil formulation. For example, a 2% minoxidil topical solution, a 3% topical minoxidil solution, a 5% topical minoxidil solution, a 5% topical minoxidil foam, a 10% topical minoxidil solution It will be understood that the ranges described above, and throughout this document, are also intended to encompass single values contained within these ranges. For example, for a formulation comprising a particular ingredient in a range between 1-50%, a percentage of 5% or 49% is also intended to be disclosed.

Therapeutic Agents

The methods of the present disclosure may be used with a nuclear receptor agonist or other compound that causes induction of sulfotransferases or PAPSS. Suitable nuclear receptor agonists can be utilized including but are not limited to, amprenavir, avasimibe, bosentan, bile acids, carbamazepine, clindamycin, clotrimazole, cortisol, cyproterone acetate, dicloxacillin, efavirenz, etoposide, dexamethasone, genistein, griseofulvin, guggulsterone, hyperforin (Saint John's Wort), indinavir, lovastatin, mifepristone, nafcillin, naringenin, nelfinavir, nifedipine, omeprazole, paclitaxel, PCBs, phenobarbital, phthalate monoesters, 5β-pregnane-3,20-dione, quercetin, rifabutin, rifampin, ritonavir, saquinavir, simvastatin, spironolactone, sulfinpyrazole, TAO, tetracycline, topotecan, transnanoclor, troglitazone, verapamil, vitamin E, vitamin K2, artemisinin, PCN, LCA, cafestol, SR-12813, rifaximin, mevastatin, TO901317, Solomonsterol A, meclizine, fibrates, WY-14,643, perfluorodecanoic acid, bile acids, GW4064, AGN29, AGN31, cafestol, fexaramine, XL335, WAY-362450, FXR-450, obeticholic acid (OCA), PX 20350, and DY 268. Additionally, derivatives of nuclear receptor agonists can be utilized including derivatives of the compounds mentioned above. In other embodiments, a prodrug that is activated to become a nuclear receptor agonist can be utilized.

In one embodiment, the nuclear receptor agonist is hyperforin, or a pharmaceutically acceptable salt or hydrate thereof, in a composition in a concentration of 0.0025% to 40%, 0.0025% to 25% by weight, or 0.005% to 22.5% by weight, or 0.0075% to 20% by weight, or 1% to 17.5% by weight, or 1.5% to 15% by weight, or 2% to 14.5% by weight, or 2.5% to 14% by weight, or 5% to 13.5% by weight, or 7.5% to 12.5% by weight, or 8% to 12% by weight, or 8.5% to 11.5% by weight, or 9% to 11% by weight, or 9.25% to 10.75% by weight, or 9.5% to 10.5% by weight, or 9.6% to 10.4% by weight, or 9.7% to 10.3% by weight, or 9.8% to 10.2% by weight, or 9.9% to 10.1% by weight, or 9.95% to 10.05% by weight, or 9.96% to 10.04% by weight, or 9.97% to 10.03% by weight, or 9.98% to 10.02% by weight, or 9.99% to 10.01% by weight.

In one embodiment, the nuclear receptor agonist is a Saint John's Wort extract containing hyperforin, or a pharmaceutically acceptable salt or hydrate thereof, in a composition in a concentration of 0.0025% to 40%, 0.0025% to 25% by weight, or 0.005% to 22.5% by weight, or 0.0075% to 20% by weight, or 1% to 17.5% by weight, or 1.5% to 15% by weight, or 2% to 14.5% by weight, or 2.5% to 14% by weight, or 5% to 13.5% by weight, or 7.5% to 12.5% by weight, or 8% to 12% by weight, or 8.5% to 11.5% by weight, or 9% to 11% by weight, or 9.25% to 10.75% by weight, or 9.5% to 10.5% by weight, or 9.6% to 10.4% by weight, or 9.7% to 10.3% by weight, or 9.8% to 10.2% by weight, or 9.9% to 10.1% by weight, or 9.95% to 10.05% by weight, or 9.96% to 10.04% by weight, or 9.97% to 10.03% by weight, or 9.98% to 10.02% by weight, or 9.99% to 10.01% by weight.

In one embodiment, the nuclear receptor agonist is vitamin K2, or a pharmaceutically acceptable salt or hydrate thereof, in a composition in a concentration of 0.0025% to 40%, 0.0025% to 25% by weight, or 0.005% to 22.5% by weight, or 0.0075% to 20% by weight, or 1% to 17.5% by weight, or 1.5% to 15% by weight, or 2% to 14.5% by weight, or 2.5% to 14% by weight, or 5% to 13.5% by weight, or 7.5% to 12.5% by weight, or 8% to 12% by weight, or 8.5% to 11.5% by weight, or 9% to 11% by weight, or 9.25% to 10.75% by weight, or 9.5% to 10.5% by weight, or 9.6% to 10.4% by weight, or 9.7% to 10.3% by weight, or 9.8% to 10.2% by weight, or 9.9% to 10.1% by weight, or 9.95% to 10.05% by weight, or 9.96% to 10.04% by weight, or 9.97% to 10.03% by weight, or 9.98% to 10.02% by weight, or 9.99% to 10.01% by weight.

In one embodiment, the Nuclear receptor agonist is genistein, or a pharmaceutically acceptable salt or hydrate thereof, in a composition in a concentration at a range of 0.25%, 0.5%, 0.75%, 1%, 1.5%, 2%, 2.5%, 5%, 7.5%, 8%, 8.5%, 9%, 9.25%, 9.5%, 9.6%, 9.7%, 9.8%, 9.9%, 9.95%, 9.96%, 9.97%, 9.98%, or 9.99% by weight as the lower weight limit of the range to an upper weight limit of 10.01%, 10.02%, 10.03%, 10.04%, 10.05%, 10.1%, 10.2%, 10.3%, 10.4%, 10.5%, 10.75%, 11%, 11.5%, 12%, 12.5%, 13.5%, 14%, 14.5%, 15%, 17.5%, 20%, 22.5%, 25%, 30%, 35%, 40%, 45%, or 50% by weight (e.g., a range of 0.25% to 10.01%, 0.25% to 10.02%, 0.5% to 10.01%, 0.5% to 10.02%, etc.).

In some embodiments, provided herein is a nuclear receptor agonist formulated with a carrier or delivery vehicle optimized for delivery of the nuclear receptor agonist to the scalp. A nuclear receptor agonist can be released using several different formulations or release methods including time release, creams, ointments, sprays, capsules, or other release methods. For instance the nuclear receptor agonist can be incorporated into a shampoo for utilization during showering. In other embodiments, the nuclear receptor agonist can be included in ointments or other topical creams that could be applied to the scalp so that it can be slowly absorbed into the skin. In other embodiments, the Nuclear receptor agonist can be included in a liquid spray or aerosol medium to be applied to the scalp. In other embodiments, the nuclear receptor agonist can be incorporated into capsules or other slow release vehicles that would allow the chemical or agent to be slowly released into the dermis of the scalp. Capsules or vehicles that encapsulate the nuclear receptor agonist can include, but are not limited to, liposomes, non-ionic liposomes, niosomes, novasome I, erythromycin-Zn complex, microspheres, nanoparticles, solid lipid nanoparticles, and nanoemulsions. In some embodiments, this can include a gel or foam that is applied to the scalp. It is specifically contemplated that the nuclear receptor agonist can be formulated in hair care products such as a shampoo, styling gel, styling foam, hair conditioner, hair serum, a hair mask, etc.

In some embodiments, provided herein is alkalinizing agent or an alkalinizing agent with a penetration enhancer formulated with a carrier or delivery vehicle optimized for delivery of the alkalinizing agent to the scalp. An alkalinizing agent can be released using several different formulations or release methods including time release, creams, solutions, lotions, serums, ointments, sprays, capsules, or other release methods. For instance the alkalinizing agent can be incorporated into a shampoo for utilization during showering. In other embodiments, the alkalinizing agent can be included in ointments or other topical creams that could be applied to the scalp so that it can be slowly absorbed into the skin. In other embodiments, the alkalinizing agent can be included in a liquid spray or aerosol medium to be applied to the scalp. In other embodiments, the alkalinizing agent can be incorporated into capsules or other slow release vehicles that would allow the chemical or agent to be slowly released into the dermis of the scalp. Capsules or vehicles that encapsulate the alkalinizing agent or an alkalinizing agent with a penetration enhancer can include, but are not limited to, liposomes, non-ionic liposomes, niosomes, novasome I, erythromycin-Zn complex, microspheres, nanoparticles, solid lipid nanoparticles, and nanoemulsions. In some embodiments, this can include a gel or foam that is applied to the scalp. It is specifically contemplated that the alkalinizing agent or an alkalinizing agent with a penetration enhancer can be formulated in hair care products such as a shampoo, styling gel, styling foam, hair conditioner, hair serum, a hair mask, etc.

In some embodiments, provided herein is acidifying agent or an acidifying agent with a penetration enhancer formulated with a carrier or delivery vehicle optimized for delivery of the acidifying agent to the skin. An acidifying agent can be released using several different formulations or release methods including time release, creams, ointments, sprays, capsules, solutions, deodorants (solid or liquid), antiperspirants (solid or liquid), moisturizers, shaving creams, shaving gels, lotions or other release methods. For instance the acidifying agent can be incorporated into an antiperspirant to use under the arms. In other embodiments, the acidifying agent can be included in moisturizer lotions or other topical creams that could be applied to the legs so that it can be slowly absorbed into the skin. In other embodiments, the acidifying agent can be included in a shaving gel that can be applied into the beard. In other embodiments, the acidifying agent can be incorporated into capsules or other slow release vehicles that would allow the chemical or agent to be slowly released into the dermis of the skin. Capsules or vehicles that encapsulate the acidifying agent or an acidifying agent with a penetration enhancer can include, but are not limited to, liposomes, non-ionic liposomes, niosomes, novasome I, erythromycin-Zn complex, microspheres, nanoparticles, solid lipid nanoparticles, and nanoemulsions. In some embodiments, this can include a gel or foam that is applied to the skin. It is specifically contemplated that the acidifying agent or an acidifying agent with a penetration enhancer can be formulated in skin care products such as a moisturizer lotion, deodorant, antiperspirant, moisturizers, shaving creams, shaving gels, etc.

Any of the aforementioned formulations can be used routinely, e.g., once daily, twice daily, every other day, once a week. Routine use of the nuclear receptor agonist, alkalinizing agent, and/or an alkalinizing agent, with or without a penetration enhancer, would be indicated as an adjuvant therapy for minoxidil in androgenetic alopecia patients. In is specifically envisioned that a composition (e.g., a shampoo) of any of the aforementioned nuclear receptor agonists, alkalinizing agent, and/or an alkalinizing agent can be used daily by a person using minoxidil to increase the effectiveness of minoxidil.

Use of RXR, RAR, and other NR agonists

Embodiments of the invention can involve use of retinoid X receptor (RXR) agonists, retinoic acid receptor (RAR) agonists, and/or an agonist of another nuclear receptor (NR) in an RXR—NR heterodimer. For example, any one or combination of RXR agonists, RAR agonists, and/or an agonist of another NR in an RXR—NR heterodimer can be used to treat or prevent hair loss (e.g., forms of alopecia), increase or improve hair growth, induce sulfotransferase, increase the efficacy of minoxidil, and/or convert androgenetic alopecia patients who are non-responders to minoxidil into responders. This can be achieved by using any one or combination of RXR agonists, RAR agonists, and/or an agonist of another NR in an RXR—NR heterodimer in accordance with any of the methods disclosed herein. As a non-limiting example, embodiments can involve use of an RXR agonist, a RAR agonist, and/or a RXR agonist with an agonist of another NR in an RXR—NR heterodimer to induce the expression of SULT1A1.

The retinoid X receptor (RXR) is an essential member of the steroid/thyroid hormone superfamily of nuclear receptors (NRs) that predominately function as transcription factors. The natural ligand of RXR was first proposed to be 9-cis-retinoic acid (9-cis-RA). However, many groups have been unable to detect endogenous 9-cis-RA in cells. All trans-retinoic acid (ATRA) had been discovered to be a ligand of RXR. Polyunsaturated fatty acids (PUFAs), such as docosahexaenoic acid (DHA) and a saturated metabolite of chlorophyll, phytanic acid are also identified as RXR ligands.

In the nucleus, RXR functions as a transcription factor. It binds to specific six-base-pair sequences of DNA in the promoter regions of genes. RXR functions as a dimer with either itself (homodimer) or another NR (heterodimer). Binding by the ligand of the NR partner defines the promoter site response element (RE) composed of two six base-pair sequences (half-sites) separated by a discrete number of bases to which the RXR—NR heterodimer binds.

Transcriptional activation by RXR—NR dimers can be classified into three categories: nonpermissive, permissive, and conditionally permissive heterodimers of RXR and another nuclear receptor (NR).

Examples of transcriptional activation by a nonpermissive heterodimeric partner include thyroid hormone receptor (TR) or vitamin D receptor (VDR). The nonpermissive NR is dominant so that binding by its agonist controls the transcriptional complex to initiate gene transcription from the nonpermissive-ligand responsive gene transcriptional start site. Binding of an RXR agonist would not enhance the response induced by the bound NR agonist.

Examples of transcriptional activation by a permissive RXR heterodimeric partner include pregnane x receptor (PXR), constitutive androstane receptor (CAR), farnesoid (bile acid) X receptor (FXR), liver (oxysterol) X receptor (LXR), and peroxisome proliferator-activated receptor (PPAR). An agonist of either partner in the heterodimeric pair such as RXR—PPAR could bind its own NR initiate gene transcription. Binding of an agonist to the second NR in the dimer would enhance the transcriptional response induced by first NR-agonist complex either additively or synergistically.

Examples of transcriptional activation by the conditionally permissive heterodimeric partner can include retinoic acid receptor (RAR). Binding of the RAR agonist would control the transcriptional response and also permit the binding of an RXR agonist. Thus, the RAR-agonist complex would be permissive. The RXR-agonist complex would then enhance the transcriptional response induced by the RAR agonist.

As such, a ligand of either RXR or a NR may be used to initiate transcription of genes. Additionally, in the case of permissive and conditionally permissive transactivation, ligands of RXR or the NR can act synergistically to activate transcription.

In one embodiment of the present invention, a RXR agonist is used to induce the expression of SULT1A1. Examples of RXR agonists include but are not limited to 9-cis-retinoic acid, all trans retinoic acid, ATRA, retinol (or retinal or retinaldehyde), retin-A, (E)-5,8,11,14,17,20-docosahexaenoic acid, lithocholic acid, phytanic acid, 9cUAB30, AGN194204, CD3254L, G100268, LG101305, methoprene acid, PA024, SR11217, SR11237 (BMS649), DEC1, DR5III, PRIC295, bexarotene, CD3254, decosahexaenoic, flurobexarotene, LG 100268, LG 100754, isotretinoin, etc.

In another embodiment of the present invention, a RAR agonist is used to induce the expression of SULT1A1.

Examples of RAR agonists include but are not limited to all-trans-retinoic acid, ATRA, retinol (or retinal or retinaldehyde), retin-A, 9-cis-retinoic acid, all-trans-5,6-epoxy retinoic acid, DR5III, isotretinoin, AC 261066, AC 55649, adapalene, AM 580, AM 80, BMS 753, BMS 961, BMS 453, CD 1530, CD 2314, CD 437, Ch 55, tazarotene, TTNPB, AR-7, FOXO1, SMRT, N-CoR, SMRTER, EC 19, etc.

In yet another embodiment of the present invention, a compound that may be metabolized by enzymes in the skin to become a RAR or RXR agonist is used to induce the expression of SULT1A1. Examples of a compound that will be metabolized to become agonists include but are not limited retinyl propionate, retinyl palmitate, or retinyl acetate.

In yet another embodiment of the present invention, a RXR agonist is used with an agonist of another NR in an RXR—NR heterodimer to induce the expression of SULT1A1. Examples of other NRs include thyroid hormone receptor (TR), vitamin D receptor (VDR), pregnane x receptor (PXR), constitutive androstane receptor (CAR), farnesoid (bile acid) X receptor (FXR), liver (oxysterol) X receptor (LXR), peroxisome proliferator-activated receptor (PPAR), retinoic acid receptor (RAR), aryl hydrocarbon receptor (AhR), Nrf2, GR, etc.

In one embodiment, the invention concerns up-regulating the sulfonating capacity of hair bearing skin, hair follicles, and/or keratinocyte cells by applying a topical solution containing a salt of minoxidil such that the one ion of the salt is an alkalinizing agent that will raise the intracellular pH of cells in the outer root sheath of the hair follicle and the counter ion is minoxidil. Examples of alkalinizing slats of minoxidil include, but are not limited to, minoxidil bicarbonate, minoxidil citrate, minoxidil carbonate, minoxidil lactate, and minoxidil acetate. In one embodiment the salt is formulated with a penetration enhancer.

The therapeutic agents, particularly an alkalinizing agent, described herein and used in the present methods may be formulated into compositions according to the knowledge of one of skill in the art. In one embodiment, the alkalinizing agents or other inducer of sulfotransferase is encapsulated in order to increase the water solubility of the therapeutic agent. In one embodiment, the alkalinizing agents or other inducer of sulfotransferase is encapsulated in order to decrease the water solubility of the therapeutic agent. In another embodiment, the alkalinizing agents or other inducer of sulfotransferase is encapsulated in order to reduce the loss through degradation of therapeutic agent, for example, to reduce oxidation of the therapeutic agent. In another embodiment, the alkalinizing agents or other inducer of sulfotransferase is encapsulated in order to promote penetration through the stratum corneum. In some embodiments the alkalinizing agent is placed in a liposome containing lecithin.

Efficacy of treatment to treat or prevent androgenetic alopecia can be determined by monitoring the density of hairs on a given area of the subject's body, e.g., a given area of the scalp. If the rate of hair loss is reduced, e.g., by 10% or more following treatment, the treatment is effective for the prevention of androgenetic alopecia. Similarly, if hair density remains the same, the treatment is effective for the prevention of androgenetic alopecia. If the density of hair increases, e.g., by 5% or more, e.g., by 10% or more following treatment, the treatment is also considered effective for the treatment and/or prevention of androgenetic alopecia.

Efficacy of treatment to treat or prevent androgenetic alopecia can be determined by monitoring global photography. For example, the patient or an expert can assess the treatment response utilizing before and after global photographs.

As noted above, it is contemplated that all forms of alopecia can benefit from the technology described herein. For example, the technology described herein can be applicable to prevent or treat androgenic alopecia.

Any of the activators, inducers, and/or inhibitors disclosed herein can be formulated as an agent (e.g., a therapeutic agent) to be used as an embodiment of a composition for implementing an embodiment of a treatment disclosed herein.

Any of the compositions, activators, inducers, inhibitors, and/or agents disclosed herein can be configured to be administered topically in the form of a shampoo, solution, foam, lotion, gel, spray, or gas. In addition, or in the alternative, any of the compositions and/or agents discloses herein can be administered orally, sublingually, by injection, as an implant, or by using a bacteria that secrets an embodiment of the agent.

Embodiments of the treatments disclosed herein can involve administration of an embodiment of the compositions, activators, inducers, inhibitors, and/or agents disclosed herein in any frequency (e.g., once daily, twice daily, every other day, weekly, monthly, etc.).

Embodiments of any of the compositions or agents disclosed herein can be applied at a predetermined frequency (e.g., once or twice per day, once per 24 hours, once per 12 hours, once per 6 hours, etc.), administered orally, injected (e.g., injected as a slow release formulation), or provided as an implant.

In one embodiment of the present invention an embodiment of the composition or therapeutic agent (e.g., any of the agents or compounds disclosed herein) that up-regulates the sulfonating capacity of hair bearing skin is delivered as a slow releasing injectable or implant. Examples of types of delivery systems include but are not limited to microparticle-based depot formulations, nanoparticle-based depot formulations, transdermal systems, or implants.

In one embodiment of the present invention an embodiment of the composition or therapeutic agent (e.g., any of the agents or compounds disclosed herein) that up-regulates the sulfonating capacity of hair bearing skin is delivered as a microparticle-based depot formulation. The formulation can include a polymeric material (e.g., biodegradable) that allows for protection of the drug cargo and control over drug release. Examples of polymer choices include but are not limited to poly(lactic-co-glycolic) acid (PLGA), poly(lactic acid) (PLA) and polyglycolic acid (PGA).

In one embodiment of the present invention an embodiment of the composition or therapeutic agent (e.g., any of the agents or compounds disclosed herein) that up-regulates the sulfonating capacity of hair bearing skin is delivered as a nanoparticle-based depot formulation. The nanoparticle-based depot formulation may contain polymeric nanoparticles, made from biocompatible and biodegradable materials, gelatin, albumin, synthetic polymers (polylactides, polyalkylcyanoacrylates), or liposomes. Nanoparticles may be synthesized from a variety of available polymers including but not limited to polylactide—polyglycolide copolymers, polyacrylates, polycaprolactones, albumin, gelatin, alginate, collagen, chitosan, polylactides, and poly (DL-lactide-co-glycolide) polymers. Nanoparticles may also include silica nanoparticles, quantum dots, metal nanoparticles (e.g., gold, Cd, Se, ZnS, or iron oxide), or lanthanide nanoparticles.

In one embodiment of the present invention an embodiment of the composition or therapeutic agent (e.g., any of the agents or compounds disclosed herein) that up-regulates the sulfonating capacity of hair bearing skin is delivered as an implant that can be either passive or active. In one embodiment, the passive drug delivery system can tune drug release from the reservoir by controlling rates of diffusion, osmosis, or concentration gradients. In one embodiment, an active drug delivery system (implant) can control drug release using a pump that can be activated by a number of methods ranging from simple manual actuation from physical pressure to electrochemically driven mechanisms that can vary drug delivery rates.

In one embodiment of the present invention an embodiment of the composition or therapeutic agent (e.g., any of the agents or compounds disclosed herein) that up-regulates the sulfonating capacity of hair bearing skin is delivered as a slow releasing suspension, liposome, in situ gel-forming system, microsphere, non-aqueous solution/suspension, or implant.

In one embodiment of the present invention an embodiment of the composition or therapeutic agent (e.g., any of the agents or compounds disclosed herein) that up-regulates the sulfonating capacity of hair bearing skin is delivered as a slow releasing injectable or implant daily, weekly, monthly, or quarterly.

In one embodiment of the present invention an embodiment of the composition or therapeutic agent (e.g., any of the agents or compounds disclosed herein) that up-regulates the sulfonating capacity of hair bearing skin is prepared as a slow releasing agent by acylation (albumin binder), carbohydrate analogue attachment, poly amino acid fusion, PEGylation, Albumin or Fc Fusion (FcRn recycling).

In yet another embodiment of the present invention, minoxidil and an embodiment of the composition or therapeutic agent (e.g., any of the agents or compounds disclosed herein) that up-regulates the sulfonating capacity of hair bearing skin are delivered together as a slow releasing injectable or implant.

In yet another embodiment minoxidil and an embodiment of the composition or therapeutic agent (e.g., any of the agents or compounds disclosed herein) that up-regulates the sulfonating capacity of hair bearing skin are delivered together as a microparticle-based depot formulation, nanoparticle-based depot formulation, transdermal system, or implant.

Embodiments of the treatments disclosed herein can involve administration of an embodiment of the compositions, activators, inducers, inhibitors, and/or agents disclosed herein for up-regulating the sulfonating capacity of hair bearing skin, hair follicles, and/or keratinocyte cells, increasing minoxidil response, converting minoxidil non-responders to responders, and/or accelerating minoxidil response.

One skilled in the art will appreciate with the benefit of the present disclosure that any one or combination of the treatment methods disclosed herein can be used in combination with any other treatment method. In addition, treatment methods can be used in various permutations. For instance, a treatment method can involve administration of a first composition selected to: up-regulate the sulfonating capacity of hair bearing skin, hair follicles, and/or keratinocyte cells; increase minoxidil response; convert minoxidil non-responders to responders; and/or accelerate minoxidil response by a first technique (e.g., inhibiting Keap 1) and then a subsequent administration of a second composition selected to: up-regulate the sulfonating capacity of hair bearing skin, hair follicles, and/or keratinocyte cells; increase minoxidil response; convert minoxidil non-responders to responders; and/or accelerate minoxidil response by a second technique (e.g., increasing the activity of p300/CBP). As a non-limiting example, a treatment method can involve administration of a first composition including a Keap 1 inhibitor agent for a first period of time (e.g., 1 week, 1 month, etc.), followed by an application of a second composition including an agent for increasing the activity of p300/CBP for a second period of time (e.g., 1 week, 1 month, etc.). One skilled in the art can appreciate that other treatment methods, periods of time, frequencies of administration, methods of administration, etc. can be used as variables in the combinations and permutations that make up the overall treatment method.

This disclosure uses the terms optical density (OD) and absprbance units (AU) interchangeably.

The various methods and techniques described above provide a number of ways to carry out the invention. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Certain embodiments of this application are described herein. Variations on those embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that can have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

EXAMPLES

Example 1: In-vitro Evaluation of Sulfotransferase Up-Regulation

The following experiment was conducted to assess the up-regulation of sulfotransferase in hair follicles by candidate compounds know to interact with human nuclear receptors (e.g., PXR and CAR).

Method: For each compound tested, 24 hairs were plucked from a human subject. Hairs were visually inspected to confirm the presence of the hair bulb. 2 hairs were placed in to 12 clean sample tubes (i.e., two hairs per reaction) containing 100 uL of Williams' E media with 0.292 g/L L-glutamine. Suitable candidate compounds were dissolved in DMSO such that when 1 uL of the compound solution was added to the sample media the final concentration of the compound was the concentration being studied (listed in the Results section). 1 uL of DMSO with no compound was added to control samples. Hairs were allowed to incubate with the candidate compounds for 24 h at room temperature. All samples were run in triplicate, i.e., the data describe in the result section is an average of three samples tested.

After 24h of incubation hairs were removed from the sample media and washed briefly with clean water. Hairs were trimmed to a length of ~1 cm and immersed, bulb first, in 100 µL of an assay solution containing 50 mM phosphate buffer (pH8), 5 mM potassium p-nitrophenyl sulfate, 20 µM adenosine 3',5'-diphosphate, 100 µM minoxidil and 5 mM MgCl2. Hairs were allowed to react with the solution for 24 hours at room temperature. After incubation, hairs were removed and the optical absorbance of the solution at 405 nm was determined with a spectrophotometer using a single scan and 1 cm path length.

Results:

TABLE 1

Up-Regulation of Sulfotransferase Via Interaction
With Human Nuclear Receptors

Patient: AB-001 Time (hrs): 24

|  |  | Control ODs: | | | | |
|---|---|---|---|---|---|---|
|  |  | OD 405 (1) | OD 405 (2) | OD 405 (3) | Average | STDEV |
|  |  | 0.121 | 0.111 | 0.127 | 0.120 | 0.008 |
| Drugs | Vitamin K2 |  |  |  |  |  |
|  | 5 uM | 0.176 | 0.211 | 0.173 | 0.187 | 0.021 |
|  | 10 uM | 0.339 | 0.138 | 0.180 | 0.219 | 0.106 |
|  | 20 uM | 0.145 | 0.208 | 0.144 | 0.166 | 0.037 |
|  |  | 0.118 | 0.337 | 0.267 | 0.241 | 0.112 |
| Drugs | Genistein |  |  |  |  |  |
|  | 10 uM | 0.186 | 0.235 | 0.134 | 0.185 | 0.051 |
|  | 25 uM | 0.179 | 0.144 | 0.085 | 0.136 | 0.048 |
|  | 50 uM | 0.122 | 0.080 | 0.190 | 0.131 | 0.056 |

TABLE 2

Up-Regulation of Sulfotransferase Via Interaction
With Human Nuclear Receptors

Patient: AB-001 Time (hrs): 24

|  |  | Control ODs: | | | | |
|---|---|---|---|---|---|---|
|  |  | OD 405 (1) | OD 405 (2) | OD405 (3) | Average | STDEV |
|  |  | 0.273 | 0.132 | 0.179 | 0.195 | 0.072 |
| Drugs | Hyperforin |  |  |  |  |  |
|  | 0.2 uM | 0.411 | 0.360 | 0.298 | 0.356 | 0.057 |
|  | 1 uM | 0.475 | 0.402 | 0.369 | 0.415 | 0.054 |
|  | 5 uM | 0.523 | 0.506 | 0.489 | 0.506 | 0.017 |

Conclusions: Hyperforin, genistein, and vitamin K2 all induced sulfotransferase activity in plucked hair follicles.

Example 2

A study was conducted on thirty human subjects (30 men) with low sulfotransferase activity as determined by colorimetric enzymatic test described by Goren et al. Subjects were recruited based on an enzymatic test result of OD<0.4 The subjects were randomized to an active group and a placebo group in a 1:1 ratio. All subjects applied 5% topical minoxidil once daily. The active group applied a shampoo containing hyperforin once a day prior to the use of minoxidil. The placebo group applied a vehicle shampoo. At the end of 1 week the average sulfotransferase activity of all subjects increased almost 3 fold (287%). The average sulfotransferase activity remained high for a follow-up period of 6 months. At 4 months, the average increase in hair counts in the active group was 166% higher than the placebo. In addition, 60% of the subjects in the active group responded to minoxidil compared to 0% of the placebo group. This demonstrates that embodiments of the method and compositions disclosed herein can convert androgenetic alopecia pateints who are non-responders to minoxidil into responders.

Example 3

A study was conducted on thirty human subjects (30 women) with low sulfotransferase activity as determined by colorometirc enzymatic test described by Goren et al. Subjects were recruited based on an enzymatic test result of OD<0.4 The subjects were randomized to an active group and a placebo group in a 1:1 ratio. All subjects applied 5% topical minoxidil once daily. The active group applied a shampoo containing hyperforin once a day prior to the use of minoxidil. The placebo group applied a vehicle shampoo. At the end of 1 week the average sulfotransferase activity of all subjects increased almost 3 fold (279%). The average sulfotransferase activity remained high for a follow-up period of 6 months. At 6 months, the average increase in hair counts in the active group was 151% higher than the placebo. In addition, 60% of the subjects in the active group responded to minoxidil compared to 0% of the placebo group. This demonstrates that embodiments of the method and compositions disclosed herein can convert androgenetic alopecia pateints who are non-responders to minoxidil into responders.

Example 4

A study was conducted on thirty human subjects (30 men) with low sulfotransferase activity as determined by colorometirc enzymatic test described by Goren et al. Subjects were recruited based on an enzymatic test result of OD<0.4 The subjects were randomized to an active group and a placebo group in a 1:1 ratio. All subjects applied 5% topical minoxidil once daily. The active group applied a shampoo containing St. John Wort once a day prior to the use of minoxidil. The placebo group applied a vehicle shampoo. At the end of 1 week the average sulfotransferase activity of all subjects increased almost 3 fold (175%). The average sulfotransferase activity remained high for a follow-up period of 6 months. At 4 months, the average increase in hair counts in the active group was 123% higher than the placebo. In addition, 60% of the subjects in the active group responded to minoxidil compared to 0% of the placebo group. This demonstrates that embodiments of the method and compositions disclosed herein can convert androgenetic alopecia pateints who are non-responders to minoxidil into responders.

Example 5

A study was conducted on thirty human subjects (30 women) with low sulfotransferase activity as determined by colorometirc enzymatic test described by Goren et al. Subjects were recruited based on an enzymatic test result of OD<0.4 The subjects were randomized to an active group and a placebo group in a 1:1 ratio. All subjects applied 5% topical minoxidil once daily. The active group applied a shampoo containing St. John Wort once a day prior to the use of minoxidil. The placebo group applied a vehicle shampoo. At the end of 1 week the average sulfotransferase activity of all subjects increased almost 3 fold (302%). The average sulfotransferase activity remained high for a follow-up period of 6 months. At 6 months, the average increase in hair counts in the active group was 142% higher than the placebo. In addition, 60% of the subjects in the active group responded to minoxidil compared to 0% of the placebo group. This demonstrates that embodiments of the method and compositions disclosed herein can convert androgenetic alopecia pateints who are non-responders to minoxidil into responders.

Example 6

A study was conducted to evaluate the efficacy of AB-103 (AB-103 formula is a combination of RXR+NR (nuclear receptors)) as an adjuvant therapy to 5% topical minoxidil solution in the treatment of Male Pattern Hair Loss (MPHL).

Methodology: Double blinded, head-to-head prospective study.

Number of Patients: 48 male subjects

Diagnosis and Inclusion Criteria:

Subject diagnosed by a dermatologist with male pattern hair loss (AGA)

Age: 18 and above

Subjects are able to give informed consent

Test product: AB-103 daily shampoo administered concomitantly with topical 5% minoxidil solution, b.i.d.

Duration of treatment: 16 weeks

Reference therapy, dose and mode of administration: Vehicle shampoo administered concomitantly with topical 5% minoxidil solution, b.i.d.

Criteria for evaluation:

Efficacy:

Each subject's global photographs before and after treatment were assessed for hair growth by a blinded expert. The assessment was made using a standardized 7 point rating scale [baseline, week 8, week 16].

The activity of the sulfotransferase enzyme from each subject's plucked hair was measured utilizing the Minoxidil Response Test [baseline, week 1, week 16].

Safety:

Each subject's scalp was evaluated by the site investigator for irritation, sensitization, erythema or any other abnormal dermatological finding [baseline, week 1, week 8, week 16].

Statistical methods: The statistical method chosen to describe the data is the Mann-Whitney U test.

Summary—Conclusions:

Efficacy Results

The aim of the study was to evaluate the efficacy of AB-103 as an adjuvant therapy to 5% topical minoxidil solution in the treatment of MPHL. A head-to-head prospective clinical study of 48 subjects treated for a minimum of 16 weeks was conducted. Subjects were randomized to two treatment arms: AB-103 administered concomitantly with topical minoxidil (treatment arm) or a vehicle shampoo administered concomitantly with topical minoxidil (comparator arm). Global photographers were evaluated by a blinded expert. The treatment response was rated on a 7 point scale as follows: −3 (significantly worse), −2 (moderately worse), −1 (slightly worse), 0 (no change), +1 (slightly improved), +2 (moderately improved) and +3 (significantly improved). The raw data from the CRFs was tabulated and graphed by an expert (refer to FIG. 1).

Eight subjects from the treatment arm and five subjects from the comparator arm did not complete the study. No reason was given for discontinuation; however, at the one week post discontinuation follow-up call none of these subjects reported adverse events. In total, 35 subjects completed the study.

The Mann-Whitney U test (MedCalc v18.2.1) was used to determine the effect of AB-103 as an adjuvant minoxidil therapy in the treatment arm versus the vehicle shampoo in the comparator arm. The null and alternate hypothesis are given below:

$H_0$: The distributions of the subjects' treatment response in the treatment arm and the comparator arm are equal $H_A$: The distributions of the subjects' treatment response in the treatment arm and the comparator arm are not equal The results indicate the following:

Mann-Whitney U test (two-sided)

Mann-Whitney U=93.5, p-value=0.0432; thus, the null hypothesis is rejected.

Safety Results: No adverse events were reported in either arm.

Conclusion:

The distributions of the subjects' treatment response in the AB-103+minoxidil arm and the vehicle shampoo+minoxidil arm were significantly different (p-value=0.0432). In the AB-103+minoxidil arm 75% of subjects experienced hair growth versus 48% in the vehicle shampoo+minoxidil arm.

Note: In this sample population, the rate of response in the comparator arm (48%) was larger than one would expect from prior clinical studies (39%). While it is possible that the vehicle improved some subjects response, it is more likely that the higher response rate observed is due to the study's small population size.

Example 7

A study was conducted to evaluate the efficacy of AB-103 in up-regulating the minoxidil sulfotransferase enzymes in human hair follicles in-vivo.

Methodology: Double blinded, placebo controlled prospective study.

Number of Patients: 20 female subjects

Diagnosis and Inclusion Criteria:

Subject diagnosed by a dermatologist with female pattern hair loss

Age: 18 and above

Subjects are able to give informed consent

Test product: AB-103 daily washout shampoo, q.d.

Duration of treatment: 7 days

Reference therapy, dose and mode of administration: Vehicle shampoo (Placebo), q.d.

Criteria for evaluation:

Efficacy:

The activity of the sulfotransferase enzyme from each subject's plucked hair was measured utilizing the Minoxidil Response Test [baseline, day 7].

Safety:

Each subject's scalp was evaluated by the site investigator for irritation, sensitization, erythema or any other abnormal dermatological finding [baseline, day 7].

Statistical methods:

The statistical method chosen to describe the data is the independent samples t-test.

Summary—Conclusions:

Efficacy Results

Figure 2:
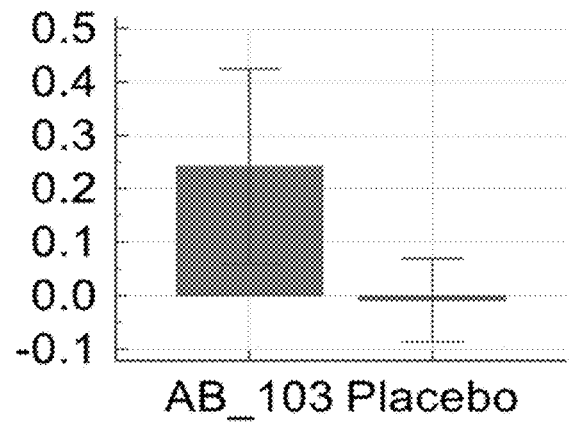
FIG. 2 is tabulated sulfotransferase enzyme activity data and a mean change in follicular sulfotransferase activity graph for a study conducted to evaluate an embodiment of AB-103 for up-regulating minoxidil sulfotransferase enzymes.

The aim of the study was to evaluate the efficacy of AB-103 in up-regulating the minoxidil sulfotransferase enzymes in human hair follicles in-vivo. A double blinded, placebo controlled prospective clinical study of 20 subjects treated for 7 days was conducted. Subjects were randomized to two treatment groups: AB-103 shampoo or the shampoo vehicle. Sulfotransferase activity levels were determined utilizing the Minoxidil Response Test. The analysis was conducted with a spectrophotometer (Shimadzu UV-1700, Kyoto, Japan). The raw data from the CRFs was tabulated and graphed by an expert (refer to FIG. 2).

The independent samples t-test (MedCalc v18.2.1) was used to determine the effect of AB-103 compared to the vehicle shampoo on follicular sulfotrasnferase activity. The null and alternate hypothesis are given below:

H₀: The mean change in sulfotrasnferase activity after 7 days of treatment with AB-103 is equal to the mean sulfotrasnferase activity after 7 days of treatment with the vehicle shampoo H_A: The mean change in sulfotrasnferase activity after 7 days of treatment with AB-103 is greater then the mean sulfotrasnferase activity after 7 days of treatment with the vehicle shampoo Mathematically written as:

$$H_0: \mu\mu_1 = \mu_2$$

$$H_A: \mu_1 > \mu_2$$

The results indicate the following:
Independent samples t-test (two-sided)
The D'Agostino-Pearson test for normal distribution (MedCalc v18.2.1) accepts normality of the differences with p=0.4278.
The analysis of the dataset yielded t(18)=−2.839, p=0.0109; therefore, the results of t-test indicate that the null hypothesis is rejected and we conclude that there was a significant difference in the mean change in sulfotransferase enzyme activity between the AB-103 group (μ=0.2413, sd=−0.2562) [95% CI: 0.05807 to 0.4246] and the placebo group (μ=−0.008420, sd=−0.1085) [95% CI: −0.08602 to 0.06918].
The 95% CI for the difference in means is $0.06492 \leq \mu_b - \mu_a \leq 0.4346$ with the best estimate being the mean difference=0.2497.
Safety Results: No adverse events were reported in either group.

Conclusion:
The mean change in sulfotrasnferase activity after 7 days of treatment with AB-103 was significantly greater than the mean change following placebo treatment (p-value<0.0109). In addition, utilizing the data from report (FI-IVD-001) regulatory submission, we conclude that the increase in sulfotrasnferase activity was significantly larger then the within-subject variability of the MRT assay.

Example 8

A study was conducted to evaluate the efficacy of AB-103 as an adjuvant therapy to 5% topical minoxidil foam in the treatment of Female Pattern Hair Loss (FPHL).
Methodology: Double blinded, head-to-head prospective study.
Number of Patients: 30 female subjects
Diagnosis and Inclusion Criteria:
Subject diagnosed by a dermatologist with female pattern hair loss
Age: 18 and above
Subjects are able to give informed consent
Test product: AB-103 daily washout shampoo administered concomitantly with topical 5% minoxidil foam, q.d.
Duration of treatment: 24 weeks
Reference therapy, dose and mode of administration: Topical 5% minoxidil foam, q.d.
Criteria for evaluation:
Efficacy:
Each subject's global photographs before and after treatment were assessed for hair growth by a blinded expert. The assessment was made using a standardized 7 point rating scale [baseline, week 12, week 24].
The activity of the sulfotransferase enzyme from each subject's plucked hair was measured utilizing the Minoxidil Response Test [baseline, week 1, week 24].

Figure 3:
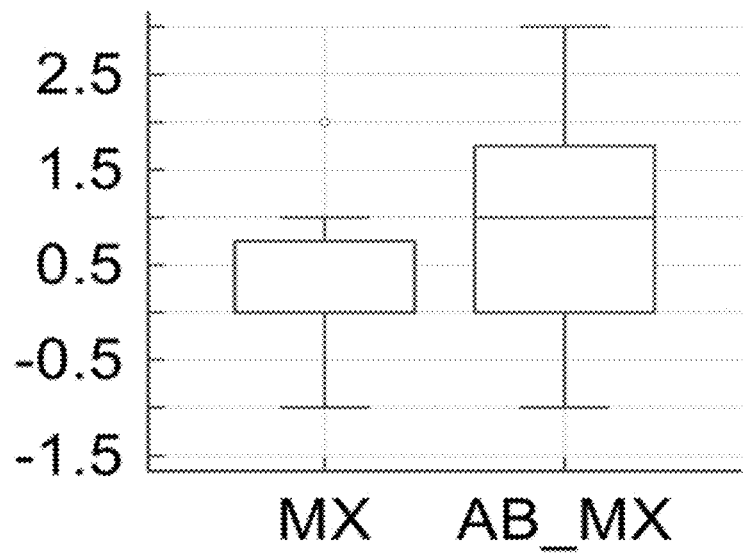
FIG. 3 is tabulated assessment of data and an expert assessment graph related to another study conducted to evaluate an embodiment of AB-103 as an adjuvant therapy.

Safety:
Each subject's scalp was evaluated by the site investigator for irritation, sensitization, erythema or any other abnormal dermatological finding [baseline, week 4, week 8, week 12, week 24].
Statistical methods:
The statistical method chosen to describe the data is the Mann-Whitney U test.
Summary—Conclusions:
Efficacy Results
The aim of the study was to evaluate the efficacy of AB-103 as an adjuvant therapy to 5% topical minoxidil foam in the treatment of FPHL. A head-to-head prospective clinical study of 30 subjects treated for a minimum of 24 weeks was conducted. Subjects were randomized to two treatment groups: AB-103 administered concomitantly with topical minoxidil or topical minoxidil mono-therapy. Global photographers were evaluated by a blinded expert. The treatment response was rated on a 7 point scale as follows: −3 (significantly worse), −2 (moderately worse), −1 (slightly worse), 0 (no change), +1 (slightly improved), +2 (moderately improved) and +3 (significantly improved). The raw data from the CRFs was tabulated and graphed by an expert (refer to FIG. 3).
The Mann-Whitney U test (MedCalc v18.2.1) was used to determine the effect of AB-103+minoxidil treatment versus minoxidil mono-therapy. The null and alternate hypothesis are given below:
H₀: The distributions of the AB-103+minoxidil group and the minoxidil mono-therapy group are equal
H_A: The distributions of the AB-103+minoxidil group and the minoxidil mono-therapy group are not equal
The results indicate the following:
Mann-Whitney U test (two-sided)
Combined Dataset (all sites): Mann-Whitney U test p-value <0.0357; thus, the null hypothesis is rejected.
Safety Results: No adverse events were reported in either group.
Conclusion:
The treatment difference between AB-103+minoxidil and minoxidil mono-therapy was statistically significant (p-value<0.0357). In the AB-103+minoxidil group 66% of subjects experienced hair growth versus 33% in the minoxidil mono-therapy group.
Albeit the small study population, this study provide initial support for the use of AB-103 as an adjuvant therapy to 5% topical minoxidil foam in the treatment of FPHL.

Example 9

A study was to evaluate the efficacy of AB-103 as an adjuvant therapy to 5% topical minoxidil foam in the treatment of FPHL patient non-responders to 5% topical minoxidil.
Methodology: Double blinded, placebo controlled prospective study.
Number of Patients: 30 female subjects
Diagnosis and Inclusion Criteria:
Subject diagnosed by a dermatologist with female pattern hair loss
Age: 18 and above
Subjects had a negative Minoxidil Response Test result (OD<0.4)
Subjects are able to give informed consent
Test product: AB-103 daily washout shampoo administered concomitantly with topical 5% minoxidil foam, q.d.
Duration of treatment: 24 weeks Reference therapy, dose and mode of administration: Vehicle shampoo administered concomitantly with topical 5% minoxidil foam, q.d.

Criteria for evaluation:

Efficacy:

Mean change in target area hair counts (TAHC) [baseline, week 24].

The activity of the sulfotransferase enzyme from each subject's plucked hair was measured utilizing the Minoxidil Response Test [baseline, week 1, week 24].

Safety:

Each subject's scalp was evaluated by the site investigator for irritation, sensitization, erythema or any other abnormal dermatological finding [baseline, week 24].

Statistical methods:

The statistical method chosen to describe the data is the independent samples t-test.

Summary—Conclusions:

Efficacy Results

Figure 4:
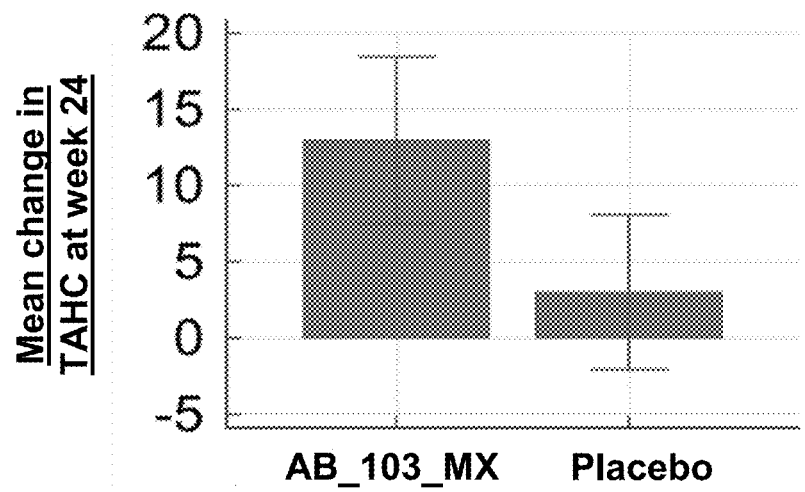
FIG. 4 is tabulated assessment of data and an assessment graph related the mean change in target area hair growth for another study conducted to evaluate an embodiment of AB-103 as an adjuvant therapy.

The aim of the study was to evaluate the efficacy of AB-103 as an adjuvant therapy to 5% topical minoxidil in the treatment of FPHL patients non-responders to 5% topical minoxidil. A double blinded placebo controlled prospective clinical study of 30 subjects treated for a minimum of 24 weeks was conducted. Subjects were randomized to two treatment groups: AB-103 administered concomitantly with topical minoxidil or a vehicle shampoo administered concomitantly with topical minoxidil (placebo group). TAHC was evaluated in a shaved and tattooed 1 cm$^2$ area of the scalp. The data from the CRFs was tabulated and graphed by an expert (refer to FIG. 4). Three subjects from the placebo group did not complete the study and one subject from the treatment group did not complete the study. No adverse events were reported in these subjects. Two of the subjects that discounted the study cited lack of visible results as a reason for discontinuation. In total, 26 subjects completed the study.

The independent samples t-test (MedCalc v18.2.1) was used to determine the mean change in TAHC in the AB-103+minoxidil group compared to the mean change in TAHC in the vehicle shampoo+minoxidil group. The null and alternate hypothesis are given below:

$H_0$: The mean change in TAHC after 24 weeks of treatment with AB-103+minoxidil is equal to the mean change in TAHC after 24 weeks of treatment with the vehicle shampoo+minoxidil $H_A$: The mean change in TAHC after 24 weeks of treatment with AB-103+minoxidil is greater than the mean change in TAHC after 24 weeks of treatment with the vehicle shampoo+minoxidil Mathematically written as:

$$H_0: \mu_1 = \mu_2$$

$$H_A: \mu_1 > \mu_2$$

The results indicate the following:

Independent samples t-test (two-sided)

The D'Agostino-Pearson test for normal distribution (MedCalc v18.2.1) accepts normality of the differences with p=0.4063.

The analysis of the dataset yielded t(24)=−2.862, p=0.0086; therefore, the results of t-test indicate that the null hypothesis is rejected and we conclude that there was a significant difference in the mean change in TAHC between the AB-103 group ($\mu$=12.9571, sd=9.4802) [95% CI: 7.4835 to 18.4308] and the placebo group ($\mu$=3.0083, sd=8.0062) [95% CI: −2.0786 to 8.0952].

The 95% CI for the difference in means is $-17.1224 \leq \mu_b - \mu_a \leq -2.7752$ with the best estimate being the mean difference=−9.9488.

Safety Results: No adverse events were reported in either group.

Conclusion:

The mean change in TAHC following 24 weeks of treatment with AB-103+minoxidil was greater than the mean change in TAHC in the placebo group (p=0.0086). Further, in the AB-103+minoxidil group 57% of subjects experienced hair growth versus 0% in the placebo group.

This study provides support for the use of AB-103 as an adjuvant therapy to 5% topical minoxidil in the treatment of FPHL patient non-responders to 5% topical minoxidil.

Example 10

Assessing the Efficacy of Alkaline pH on Increasing Collicular Sulfotransferase.

Study 001

An in-vitro study was conducted to assess the efficacy of an alkaline pH solution on increasing follicular sulfotransferase. Twenty hairs were plucked from each subject. The baseline sulfotransferase activity of each subject was measured by analyzing 10 plucked hairs with an Minoxidil Response Test devised by Goren et al. The remaining 10 hairs were incubated with an alkaline solution (pH of 8.5) for a period of 24 hour at a temperature of 37° C. Thereafter, the remaining 10 plucked hairs were analyzed with the Minoxidil Response Test devised by Goren et al. The data is summarized in Table 3 below. The average increase was approximately 100%.

TABLE 3

Efficacy of Alkaline pH on Increasing Collicular Sulfotransferase

| Subject | Baseline Activity (OD) | Post Treatment Activity (OD) |
|---|---|---|
| 1 | 0.19 | 0.374 |
| 2 | 0.87 | 1.803 |
| 3 | 0.32 | 0.521 |

Study 002

A study was conducted on thirty human subjects (30 men) with low sulfotransferase activity as determined by colorimetric enzymatic test described by Goren et al. Subjects were recruited based on an enzymatic test result of OD<0.4. The subjects were randomized to an active group and a placebo group in a 1:1 ratio. All subjects applied 5% topical minoxidil once daily. The active group applied an alkaline solution (pH of 8.5) once a day prior to the use of minoxidil. The placebo group applied a vehicle solution (pH 7.0). At the end of 1 week, the average sulfotransferase activity of all subjects increased almost 2 fold (95%). The average sulfotransferase activity remained high for a follow-up period of 6 months. At 4 months, the average increase in hair counts in the active group was 192% higher than the placebo. In addition, approximately 50% of the subjects in the active group responded to minoxidil compared to 0% of the placebo group.

Study 003

A study was conducted on thirty human subjects (30 women) with low sulfotransferase activity as determined by colorometirc enzymatic test described by Goren et al. Subjects were recruited based on an enzymatic test result of OD<0.4. The subjects were randomized to an active group and a placebo group in a 1:1 ratio. All subjects applied 5% topical minoxidil once daily. The active group applied an alkaline solution (pH of 8.5) once a day prior to the use of minoxidil. The placebo group applied a vehicle solution (pH 7.0). At the end of 1 week, the average sulfotransferase activity of all subjects increased almost 2 fold (115%). The average sulfotransferase activity remained high for a follow-up period of 6 months. At 6 months, the average increase in hair counts in the active group was 173% higher than the placebo. In addition, approximately 50% of the subjects in the active group responded to minoxidil compared to 0% of the placebo group.

Example 11 pHi Assay

Bromothymol Blue, 0.04% Aqueous solution was used as a pH indicator to visualize intracellular pH (pHi) of cells located in the Hair Follicle Stem Cell (HFSC) niche. In a neutral solution of pH 6.0-7.6 Bromothylmol Blue appears green, below pH 6.0 it appears yellow, and above pH 7.6 it appears blue. Hair follicles were submerged in assay solution for approximately 5 minutes, until HFSCs were stained. Cells were visualized using a 20× magnification stereo microscope equipped with a 5 MP Color Digital Eyepiece Microscope Camera.

TABLE 4

| Composition/Information on Ingredients | | | |
|---|---|---|---|
| Chemical Name | CAS# | % | EINICS |
| Water | 7732-18-5 | 99.96% | 231-791-2 |
| Bromothymol blue, sodium salt | 34722-90-2 | 0.04% | 252-269-7 | pHi of HFSC

The following experiment was conducted to assess the intracellular pH of the HFSC niche in hair.

Method:

1 hair was plucked from each human subject. Hairs were visually inspected to confirm the presence of the hair bulb and hairs were rinsed briefly with clean water. Hairs were then immersed, bulb first, in 100 μL of assay solution. Hairs were allowed to react with the solution for 5 minutes at room temperature. After incubation, hairs were removed and mounted on a clean glass slide and visualized using a 20× magnification stereo microscope equipped with a 5MP Color Digital Eyepiece Microscope Camera.

Figure 5:
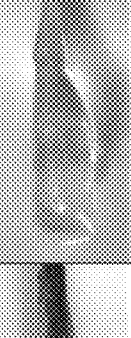
FIG. 5 is a table showing results for PHi of HFSC niche in hair follicles.
Figure 5:
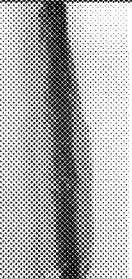

Results: See Table 5 of FIG. 5.

Conclusion: the intracellular pH of cells contained in the HFSC niche was below pH 6.0

In vitro upregulation of SULT1A1 by increasing pH (24 h)

The following experiment was conducted to assess the up-regulation of sulfotransferase in hair follicles by an increase in pHi.

Method:

For each pH tested, 36 hairs were plucked from a human subject. Hairs were visually inspected to confirm the presence of the hair bulb. 2 hairs were placed in to 9 wells (i.e., two hairs per reaction) of a sterile flat bottom tissue culture plate containing 250 uL of Williams' E media with 0.292 g/L L-glutamine at pH 5.9, 7.4, and 8.1 (i.e. 3 wells per pH). Hairs were incubated for 6 hours and 24 hours at 5% $CO_2$, 100% relative humidity. All samples were run in triplicate, i.e. the data described in the results section is an average of three samples tested for each pH.

After 24 hours of incubation, hairs were removed from the sample media and washed briefly with clean water. Hairs were trimmed to a length of ~1 cm and immersed, bulb first, in 100 μL of an assay solution containing 50 mM phosphate buffer (pH8), 5 mM potassium p-nitrophenyl sulfate, 20 μM adenosine 3',5'-diphosphate, 100 μM minoxidil and 5 mM MgCl2. Hairs were allowed to react with the solution for 24 hours at room temperature. After incubation, hairs were removed and the optical absorbance of the solution at 405 nm was determined with a spectrophotometer using a single scan and 1 cm path length.

Results: See Tables 6-7 below.

TABLE 6

| Incubation in media for 24 hour. | | | |
|---|---|---|---|
| Subject | OD 405 nm pH 5.9 | OD 405 nm pH 7.4 | OD 405 nm pH 8.1 |
| AB-011 | 0.113 | 0.118 | 0.115 |
| AB-012 | 0.088 | 0.074 | 0.080 |
| AB-013 | 0.398 | 0.406 | 0.393 |
| AB-014 | 0.444 | 0.423 | 0.446 |
| AB-015 | 0.612 | 0.622 | 0.626 |

TABLE 7

| Incubation in media for 6 hours. | | | |
|---|---|---|---|
| Subject | OD 405 nm pH 5.9 | OD 405 nm pH 7.4 | OD 405 nm pH 8.1 |
| AB-011 | 0.102 | 0.233 | 0.473 |
| AB-012 | 0.054 | 0.206 | 0.314 |
| AB-013 | 0.403 | 0.492 | 0.827 |
| AB-014 | 0.421 | 0.933 | 1.108 |
| AB-015 | 0.621 | 1.344 | 1.665 |

Conclusion: Incubating hairs in growth medium above pH 7.0 was able to significantly upregulate sulfotransferase response in 24 hours, but not in 6 hours.

In vivo change of HFSC niche pHi

The following experiment was conducted to assess the ability to change HFSC pHi by applying a topical solution to the scalp.

Method:

1 mL of 10% solution of sodium bicarbonate in Dimethyl sulfoxide (DMSO) was applied to the scalp of each subject in a small quarter-sized area. 1 hair from within the area was plucked from each subject at time 0 (zero), 15, and 30 min. Hairs were visually inspected to confirm the presence of the hair bulb and were rinsed briefly with clean water. Hairs were then immersed, bulb first, in 100 μL of assay solution. Hairs were allowed to react with the solution for 5 minutes at room temperature. After incubation, hairs were removed and mounted on a clean glass slide and visualized using a 20× magnification stereo microscope equipped with a 5MP Color Digital Eyepiece Microscope Camera.

Figure 7:
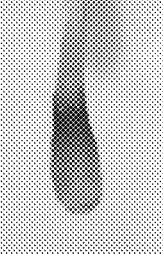
Figure 7:
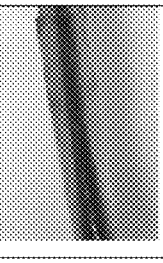
Figure 8:
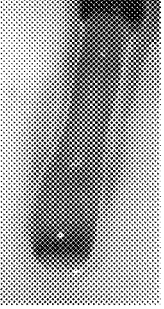
Figure 8:
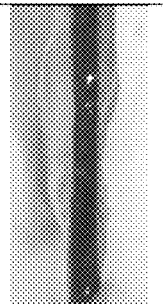

Results: See Tables 8-10 of FIGS. 6-8.

Conclusion: Topical application of 10% sodium bicarbonate in DMSO was able to change the pHi of cells located in the HFSC niche within 30 minutes of application.

Example 12

Sulfotransferase Up-regulation with Alkalizing Agents in Human Hair Follicle

Twenty-four (24) hairs were plucked from each human subject. Hairs were visually inspected to confirm the presence of the hair bulb. 2 hairs were placed in to an open 1.5 mL tube (i.e., two hairs per reaction) containing 400 µL of Dulbecco's Modified Eagle's Medium/Nutrient Mixture F-12 Ham media with 0.365 g/L L-glutamine, 1.2 g/L $NaHCO_3$, 5.18 g/L CHES, pH 9.5. Hairs were incubated for 0 (baseline), 4, 8, 16, 20, and 24 hours at 37° C., 100% relative humidity. All samples were run in quadruplicate and the experiment was repeated four times, i.e. the data described in the results section is an average of four experiments with four samples tested for each time point.

Figure 9:
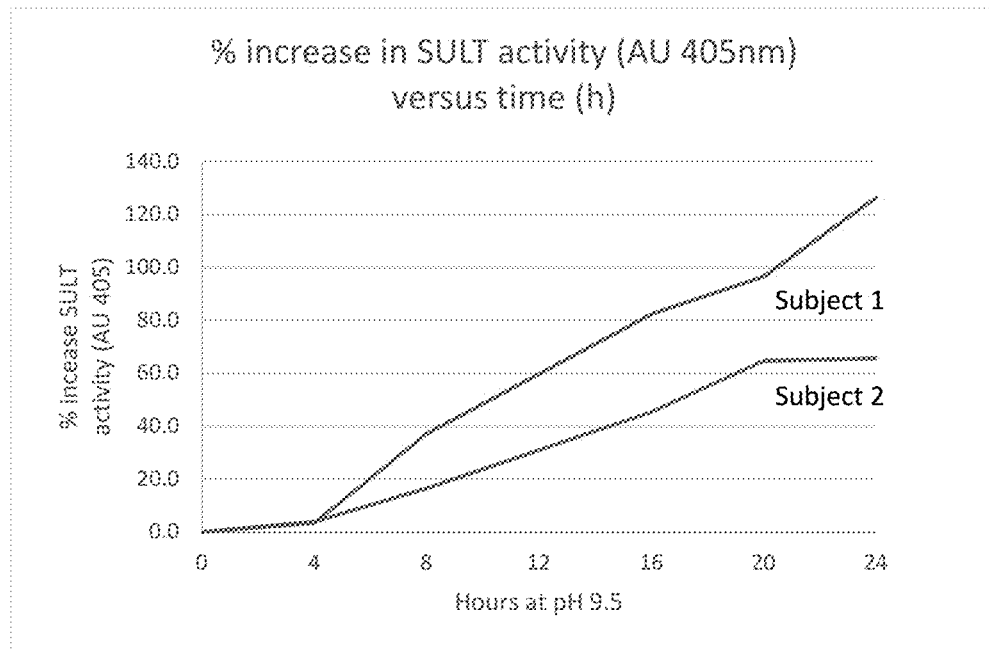
FIG. 9 shows results of % increase in activity per hour at pH 9.5 for two subjects.

After each time point of incubation, hairs were removed from the sample media and washed briefly with clean water. Hairs were trimmed to a length of ~1 cm and immersed, bulb first, in 100 µL of an assay solution containing 50 mM phosphate buffer (pH8), 5 mM potassium p-nitrophenyl sulfate, 20 µM adenosine 3',5'-diphosphate, 100 µM minoxidil and 5 mM $MgCl2$. Hairs were allowed to react with the solution for 24 hours at room temperature. Referring to FIG. 9, after incubation, hairs were removed and the optical absorbance of the solution at 405 nm was determined with a spectrophotometer using a single scan and 1 cm path length.

TABLE 8

Results of sulfotransferase up-regulation with alkalizing agents study

| Time exposed to pH 9.5 media (hrs) | AVG OD (405 nm) | % increase from baseline (0 hr) |
|---|---|---|
| Subject 1 | | |
| 0 | 0.287 | 0.0 |
| 4 | 0.297 | 3.4 |
| 8 | 0.393 | 37.1 |
| 16 | 0.523 | 82.2 |
| 20 | 0.564 | 96.5 |
| 24 | 0.649 | 126.3 |
| Subject 2 | | |
| 0 | 0.984 | 0.0 |
| 4 | 1.022 | 3.8 |
| 8 | 1.145 | 16.4 |
| 16 | 1.430 | 45.3 |
| 20 | 1.621 | 64.6 |
| 24 | 1.630 | 65.6 |

Example 13

Alkalizing Topical Formulas with and without Minoxidil

Table 9 shows various topical formulations containing a salt of minoxidil (e.g., alkalinizing salts of minoxidil) with and without Minoxidil that may be used with embodiments of the present invention.

TABLE 9

Topical formulations containing a salt of minoxidil

| Ingredient | F1 | F2 | F3 | F4 | F5 |
|---|---|---|---|---|---|
| Minoxidil | 0.00 | 5.00 | 5.00 | 5.00 | 0.00 |
| Glycerol | 18.00 | 18.00 | 10.80 | 10.80 | 18.00 |
| BHT | 0.05 | 0.05 | 0.05 | 0.05 | 0.05 |
| Ethanol | 20.70 | 45.40 | 44.90 | 47.40 | 19.70 |
| Water | 50.00 | 23.00 | 30.00 | 30.00 | 50.00 |
| Labrasol | 5.00 | 5.00 | 5.00 | 3.00 | 5.00 |
| Lecithin | 1.25 | 1.25 | 1.25 | 0.75 | 1.25 |
| $NaHCO_3$ | 5.00 | 2.30 | 3.00 | 3.00 | 5.00 |
| Span 20 | 0.00 | 0.00 | 0.00 | 0.00 | 1.00 |
| Total | 100.00 | 100.00 | 100.00 | 100.00 | 100.00 |

Example 14

Human Hair Follicle pH Changes versus Time with Topical Application of Alkalizing Topical Formulas Various topical formulations were applied to the scalp of subjects. Hairs from the application site were plucked hourly over an 24-hour period. Hairs after each pluck were imaged to detect the pH change caused by each formulation over the duration of the experiment. The pHi assay described in Example 11 was utilized to detect elevated pH. Hairs were plucked once every hour for 8 hours and then again the next day (24 h).

TABLE 10

Image results detecting pH change for plucked hairs

| | Formula F1 | | Formula F2 | | Formula F3 | | Formula F4 | |
|---|---|---|---|---|---|---|---|---|
| Time (h) | Subject 1 | Subject 2 | Subject 1 | Subject 2 | Subject 1 | Subject 2 | Subject 1 | Subject 2 |
| 1 | Blue | Blue | Yellow | Yellow | Blue | Blue | Blue | Blue |
| 2 | Blue | Blue | Yellow | Yellow | Yellow | Yellow | Blue | Blue |
| 3 | Blue | Blue | NA | NA | Yellow | Yellow | Blue | Blue |
| 4 | Blue | Blue | NA | NA | NA | NA | Blue | Blue |
| 5 | Blue | Blue | NA | NA | NA | NA | Blue | Yellow |
| 6 | Blue | Yellow | NA | NA | NA | NA | Blue | Yellow |
| 7 | Blue | Yellow | NA | NA | NA | NA | Yellow | Yellow |
| 8 | Yellow | Yellow | NA | NA | NA | NA | Yellow | Yellow |
| 24 | Yellow | Yellow | NA | NA | NA | NA | Yellow | Yellow |

The invention claimed is:

1. A composition for treating hair loss, improving hair growth, accelerating hair growth, increasing the sulfonating capacity of a hair follicle cell and/or keratinocyte cell, inducing sulfotransferase in a hair follicle, inducing expression of sulfotransferase, increasing sulfotransferase activity, increasing hair thickness and/or diameter, increasing hair growth rate, increasing hair density, accelerating hair growth, treating for alopecia, upregulating sulfotransferase, converting non-responders to minoxidil responders, and/or improving minoxidil response, the composition comprising:
an agent configured to induce expression of sulfotransferase in skin of a person exhibiting the effects of hair loss, wherein the agent includes a salt of minoxidil and an inorganic sulfur source.

2. The composition of claim 1, wherein:
the salt of minoxidil comprises a first ion and a second ion;
the first ion of the salt is an alkalinizing agent configured to raise intracellular pH of cells in an outer root sheath of a hair follicle; and
the second ion of the salt is a counter ion that is minoxidil.

3. The composition of claim 2, wherein the alkalinizing agent includes any one or combination of: minoxidil bicarbonate, minoxidil citrate, minoxidil carbonate, minoxidil lactate, and minoxidil acetate.

4. The composition of claim 1, further comprising a penetration enhancer.

5. The composition of claim 2, wherein the alkalinizing agent is encapsulated, the encapsulation configured to any one or combination of:
increase the water solubility of the composition;
decrease the water solubility of the composition;
reduce the loss through degradation of therapeutic agent; and
promote penetration through the stratum corneum.

6. The composition of claim 2, wherein the alkalinizing agent is placed in a liposome.

7. The composition of claim 1, wherein the composition is configured to be administered by applying the composition at a predetermined frequency, administering the composition orally, injecting the composition, or providing the composition as an implant.

8. The composition of claim 1, wherein the composition is configured to be administered by applying the composition at a predetermined frequency, wherein the composition further comprises a carrier, wherein the composition is formulated as any one or combination of a shampoo, a foam, ointment, spray, solution, gel, slow release capsule, oral tablet, dry shampoo, hair styling product, or exfoliating agent.

9. The composition of claim 1, wherein the composition is formulated as a cosmetic product.

10. The composition of claim 1, wherein the composition is formulated as any one or combination of a time release vehicle, a cream, a solution, a lotion, a serum, an ointment, a spray, an aerosol medium, a capsule, a shampoo, a gel, a foam, a cosmetic, a hair conditioner, a hair care product, a hair mask, a deodorant, an antiperspirant, a moisturizer, or a shaving cream or gel.

11. A kit for treating hair loss, improving hair growth, accelerating hair growth, increasing the sulfonating capacity of a hair follicle cell and/or keratinocyte cell, inducing sulfotransferase in a hair follicle, inducing expression of sulfotransferase, increasing hair thickness and/or diameter, increasing hair growth rate, increasing hair density, accelerating hair growth, treating for alopecia, upregulating sulfotransferase, converting non-responders to minoxidil responders, and/or improving minoxidil response, the kit comprising the composition of claim 1 and a dispenser, implant, or pill.

12. The kit of claim 11, wherein the composition is formulated as any one or combination of a time release vehicle, a cream, a solution, a lotion, a serum, an ointment, a spray, an aerosol medium, a capsule, a shampoo, a gel, a foam, a cosmetic, a hair conditioner, a hair care product, a hair mask, a deodorant, an antiperspirant, a moisturizer, or a shaving cream or gel.

13. The composition of claim 1, further comprising minoxidil.

14. The kit of claim 11, wherein the composition further includes minoxidil.

15. The compositions of claim 1, wherein treating for alopecia includes treating for alopecia areata, treating for chemotherapy induced alopecia, treating female and/or male pattern hair loss, and/or treating androgenetic alopecia.

16. The composition of claim 1, wherein the inorganic sulfur source is chosen from the group consisting of cysteine, L-cysteine, hydrogen sulfide, elemental sulfur, sulfite, thiosulfate, polythionates, magnesium sulfate, sodium sulfate, and sodium metabisulfite.

17. The composition of claim 6, wherein the liposome contains lecithin.

* * * * *